United States Patent [19]

Lewis et al.

[11] Patent Number: 5,714,146
[45] Date of Patent: Feb. 3, 1998

[54] IL-4 BONE THERAPY

[75] Inventors: David B. Lewis; Roger M. Perlmutter, both of Seattle, Wash.

[73] Assignee: Board of Regents of the University of Washington, Seattle, Wash.

[21] Appl. No.: 418,826

[22] Filed: Apr. 7, 1995

Related U.S. Application Data

[63] Continuation of Ser. No. 935,891, Aug. 26, 1992, abandoned.

[51] Int. Cl.$^6$ .................... C12N 15/00; A61K 39/00; A61K 39/395
[52] U.S. Cl. .................. 424/130.1; 800/2; 424/143.1; 424/145.1; 424/152.1; 424/184.1
[58] Field of Search .................. 424/184.1, 130.1, 424/143.1, 145.1, 152.1; 800/2; 435/6

[56] References Cited

U.S. PATENT DOCUMENTS

| | | | |
|---|---|---|---|
| 4,736,866 | 4/1988 | Leder et al. | 800/1 |
| 5,013,824 | 5/1991 | Abraams et al. | 530/300 |
| 5,017,691 | 5/1991 | Lee et al. | 535/351 |
| 5,041,381 | 8/1991 | Abrams et al. | 435/240 |
| 5,082,927 | 1/1992 | Pastan et al. | 530/351 |
| 5,175,383 | 12/1992 | Leder et al. | 800/2 |

FOREIGN PATENT DOCUMENTS

| | | | |
|---|---|---|---|
| WO89/09621 | 10/1989 | WIPO | A61K 39/395 |
| WO90/05183 | 5/1990 | WIPO | C12N 15/12 |
| WO91/03555 | 3/1991 | WIPO | C12N 15/12 |
| WO91/09059 | 6/1991 | WIPO | C07K 15/06 |
| WO91/13979 | 9/1991 | WIPO | C12N 15/00 |
| WO91/13984 | 9/1991 | WIPO | C12N 15/12 |
| WO91/16348 | 10/1991 | WIPO | C07K 13/00 |

OTHER PUBLICATIONS

Lehn M, W.Y. Weiser, S. Engelhorn, S. Gillis, and H.G. Remold. IL-4 inhibits $H_2O_2$ production and antileishmanial capacity of human cultured monocytes mediated by IFN-γ. J. Immunol 143:3020–3024, 1989.

Standiford T.J., R.M. Strieter, K. Kasahara and S.L. Kunkel. Disparate regulation of interleukin 8 gene expression from blood monocytes, endothelial cells, and fibroblasts by interleukin 4. Biochem. Biophys. Res. Commun. 171:531–536, 1990.

Rennick D., G. Yang, C. Muller–Sieburg, C. Smith, N. Arai, Y. Takabe, and L. Gemmell. Interleukin 4 (B–cell stimulatory factor 1) can enhance or antagonize the factor–dependent growth of hemopoietic progenitor cells. Proc. Nat'l. Acad. Sci. USA 84:6889–6893, 1987.

Lacey D.L., J.M. Erdmann, H. Suzuki, and J. Ohara. MC3T3 osteoblastic cells express receptors for and respond to interleukin–4. J. Bone Mineral Res. 6 (supplement 1):S255, 1991.

Imai Y., T. Tsunenari, M. Fukase, and T. Fujita. Quantitative bone histomorphometry and circulating T lymphocyte subsets in postmenopausal osteoporosis. J. Bone Mineral Res. 5:393–399, 1990.

Rosen C.J., K. Usiskin, M. Owens, C.O. Barlascini, M. Belsky, and R.A. Adler. T lymphocyte surface antigen markers in osteoporosis. J. Bone Mineral Res. 5:851–855, 1990.

Ernst D.N., M.V. Hobbs, B.E. Torbett, A.L. Glasebrook, M.A. Rehse, K. Bottomly, K. Hayakawa, R.R. Hardy and W.O. Weigle. Differences in the expression profiles of CD45RB, Pgp–1, and 3G11 membrane antigens and in the patterns of lymphokine secretion by splenic CD4$^+$cells from young and aged mice. J. Immunol 145:1295–1302, 1990.

Lewis D.B., K.S. Prickett, A. Larsen, K. Grabstein, M. Weaver, and C.B. Wilson. Restricted production of interleukin 4 by activated human T cells. Proc. Nat'l. Acad. Sci. USA 85:9743–9747, 1988.

Lewis D.B., C.C. Yu, J. Meyer, B.K. English, S.J. Kahn, and C.B. Wilson. Cellular and molecular mechanisms for reduced interleukin 4 and interferon–γ production by neonatal T cells. J. Clin. Invest. 87:194–202, 1991.

Pacifici R., L. Rifas, S. Teitelbaum, E. Slatopolsky, R. McCracken, M. Bergfeld, W. Lee, L.V. Avioli, W.A. Peck. Spontaneous release of interleukin 1 from human blood monocytes reflects bone formation in idiopathis osteoporosis. Proc. Nat'l Acad. Sci. USA 84:4616–4260, 1987.

Killar, L.M., C.A. Hatfield, S.R. Carding, M. Pan, G.E. Winterrowd and K. Bottomly. In vivo administration of interleukin 1 elicits increased Ia antigen expression on B cells through the induction interleukin 4. Eur. J. Immunol 19:2205–2210, 1989.

Brown, M.A., J.H. Pierce, C.J. Watson, J. Falco, J.N. Ihle, and W.E. Paul. B cell stimulatory factor–1/Interleukin–4 mRNA is expressed by normal and transformed mast cells. Cell 50:809–818, 1987.

Parfitt AM. The cellular basis of bone remodeling: The quantum concept reexamined in light of recent advances in the cell biology of bone. Calcif. Tissue Int. 36:S37–S45,1 984.

Mundy GM. Local factors in bone remodeling. Recent Prog. Hormone Res. 45:507–531, 1989.

Thomson BM, J. Saklatvala, and T.J. Chambers, J. Exp. Med. 164:104–112, 1986.

(List continued on next page.)

*Primary Examiner*—Suzanne E. Ziska
*Attorney, Agent, or Firm*—Christensen O'Connor Johnson & Kindness PLLC

[57] ABSTRACT

An in vivo assay for selecting a candidate therapeutic for treating osteoporosis. A candidate reagent is administered to an IL-4 transgenic mammal whose cells contain a recombinant IL-4 coding sequence operably lined to a promoter sequence which is transcriptionally active in bone marrow cells. At the time the candidate reagent is first administered the IL-4 transgenic mammal is either symptomatic of, or asymptomatic of, an osteoporotic phenotype. The candidate reagent is selected as a candidate therapeutic for treating osteoporosis if either amelioration of, or delay in the onset of, the osteoporotic phenotype is observed following administration of the candidate reagent to the IL-4 transgenic mammal.

1 Claim, 7 Drawing Sheets

OTHER PUBLICATIONS

Thomson BM, G.R. Mundy, and T.J. Chambers, J. Immunol 138:775–779,1987.

McSheehy PMJ, 1,25–Dihdroxyvitamin $D_3$ stimulates rat osteoblastic cells to release a soluble factor that increases osetoclastic bone resorption. J. Clin. Invest. 80:425–429, 1987.

Lewis DB, C.C. Yu, I.A. Forbush, J. Carpenter, T.A. Sato, A. Grossman, D.H. Liggitt, and R.M. Perlmutter. Interleukin 4 expressed in situ selectively alters thymocyte development. J. Exp. Med. 173:89–100, 1991.

Garvin AM, S. Pawar, J.D. Marth, and R.M. Perlmutter. Structure of the murine lck gene and its rearrangement in a murine lymphoma cell line. Mol. Cell Biol. 8:3058–3064, 1988.

Perlmutter RM, J.D. Marth, S.F. Ziegler, A.M. Garvin, S. Pawar, M.P. Cooke, and K.M. Abraham. Specialized protein tyrosine kinase proto–oncogens in hematopoietic cells. Biochim Biophys. Acta. 948:245–262, 1988.

Perlmutter RM, J.D. Marth, D.B. Lewis, R. Peet, S.F. Ziegler, and C.B. Wilson. Structure and expression of lck transcripts in human lymphoid cells. J. Cell Biochem. 38:117–126, 1988.

Marth JD, R. Peet, E.G. Krebs, and R.M. Perlmutter. A lymphocyte–specific protein–tyrosine kinase gene is rearrange and overexpressed in the murine T cell lymphoma LSTRA. Cell 43:393–404, 1985.

Shioi A, S.L. Teitelbaum, F. P. Ross, H.G. Welgus, H.Suzuki, J. Ohara, and D.L. Lacey. Interleukin 4 inhibits murine osteoclast formation in vitro. J. Cell Biochem. 45:272–277, 1991.

Hart P.H., G.F. Vitti, D.R. Burgess, G.A. Whitty, D.S. Piccoli, and J.A. Hamilton. Potential antiinflammatory effects of interleukin 4: Suppression of human monocyte tumor necrosis factor α, interleukin 1, and prostaglandin $E_2$. Proc. Natl Acad. Sci. USA 86:3803–3807, 1989.

Standiford T.J., R.M. Strieter, S.W. Chensue, J.Westwick, K. Kasahara, and S.L. Kunkel. IL–4 inhibits the expression of IL–8 from stimulated human monocytes. J. Immunol 145:1435–1439,1990.

Leung, D.Y.M. and R.S. Geha. Clinical and immunologic aspects of the hyperimmunoglobulin E syndrome. Hematol/Oncol Clin. N. Amer. 2:81–100, 1988

Vercelli, D., H.H. Jabara, C.Cunningham–Rundles, J.S. Abrams, D.B. Lewis, J. Meyer, L.C. Schneider, D.Y.M. Leung, and R.S. Geha Regulation of immunoglobulin (Ig)E synthesis in the Hypr–IgE Syndrome. J. Clin. Invest. 85:1666–1671, 1990.

Kalu, D.N., C–C. Liu, R.R. Hardin and B.W. Hollis,The Aged rat model of ovarian hormone deficiency bone loss. Endocrinology 124:7–16, 1989.

Matzsch, T., D. Bergqvist, U. Hedner, B. Nilsson, and P. Osergaard. Heparin–induced osteoporosis in rats. Thrombosis and Haemostasis 56:293–294, 1986.

Glajchen, N., F. Ismail, S. Epstein, P.S. Jowell, and M. Fallon. The effect of chronic caffeine administration on serum markers of bone mineral metabolism and bone histomorphometry int he rat. Calcif. Tissue Int. 43:277–280, 1988.

Tsuboyama, T., M. Matsushita, H. Okumura, T. Yamamuro, K. Hanada and T. Takeda. Modification of strain–specific femoral bone density by bone marrow chimerism in mice: A study on the spontaneously osteoporotic mouse (SAM–P/6). Bone 10:269–277, 1989.

Banchereau, J., T. Defrance, J.P. Galizzi, P. Miossec, and F. Rousset. Human interleukin 4. Bull Cancer (Paris) 78:299–306, 1991.

Lian, J., C. Stewart, E. Puchacz, S. Mackowiak, V. Shalhoub, D. Collart, G. Zambetti, and G. Stein. Structure of the rat osteocalcin gene and regulation of vitamin D–dependent expression. Proc. Nat'l Acad. Sci. USA 86:1143–1147, 1989.

Noma, Y., P. Sideras, T. Naito, S. Bergstedt–Lindquist, C. Azuma, E. Severinson, T. Tanabe, T. Kinashi, F. Matsuda, Y. Yaoita, and T. Honjo. Cloning of cDNA encoding the murine IgG1 induction factor by a novel strategy using SP6 promoter. Nature (Lond.) 319:640–646, 1986.

Brinster, R.L., J.M. Allen, R.R. Berhringer, R.E. Gelinas, and R.D. Palmiter. Introns increase transcriptional efficiency in transgenic mice. Proc. Nat'l Acad. Sci. USA 85:836–840, 1988.

Tepper, R.I., D.A. Levinson, B.Z. Stanger, J. Campos–Torres, A.K. Abbas, and P. Leder. IL–4 induces allergic–like inflammatory disease and alters T cell development in transgenic mice. Cell 62:457–467, 1990.

Burstein, H.J., R.I. Tepper, P. Leder, and A.K. Abbs. Humoral immune functions in IL–4 transgenic mice. J. Immunol 147:2950–2956, 1991.

Müller, W., R. Kuhn and K. Rajewsky. Major histocompatibility complex class II hyperexperssion on B cells in interleukin 4–transgenic mice does not lead to B cell proliferation and hypergammaglobulinemia. Eur. J. Immunol 21:921–925, 1991.

Biondi, A., C. Paghanin, V. Rossi, S. Benvestito, R.M. Perlmutter, A. Mantovani and P. Allavena. Expression of lineage–restricted protein tyrosine kinase genes in human natural killer cells. Eur J. Immunol 21:843–846, 1991.

Gillis, S. T–Cell–Deried Lymphokines. Fundamental Immunol. Second Ed. W.E. Paul, Raven Press Ltd., N.Y. 1989, pp. 621–638.

Allen, J.M., K.A. Forbush, and R.M. Perlmutter. Functional dissection of the lck proximal promoter. Mol. Cell. Biol. 12: 2758–2768, 1992.

Jilka, R.L., G. Hangoc, G. Girasole, G. Passeri, D.C. Williams, J. S. osteoclast deelopment after estrogen loss: mediation by interleukin–6. Science 257:88–91, 1992.

Barbolt, T.A., K.A. Gossett, and J.B. Cornacoff. Histomorphologic observations for Cynomolgus monkeys after subchronic subcutaneous injection of recombinant human interleukin–4. Toxicol Pathol. 19: 251–257.

Shioi et al., J. Cell. Biochem. 47:272, 1991.

Lewis et al. L, J. Exp. Med. 173:89, 1991.

Lewis et al J Exp Med 173:89, 1991.

Shivi et al J Cell Biochem 47:272, 1991.

Lay Abstract 686, J Bone Min Res 6: S255, 1991.

IL-4 BONE THERAPY

This is a continuation of prior application Ser. No. 07/935,891, filed Aug. 26, 1992, now abandoned which is incorporated herein by reference, and the benefit of the filing date of which is hereby claimed under 35 U.S.C. §120.

This invention was made in part with government support under grants AI/HD 26940 and AR 41657 awarded by the National Institutes of Health. The government has certain rights in the invention.

FIELD OF THE INVENTION

The invention provides animal and in vitro models for the evaluation of candidate drugs and therapies for the prevention and treatment of bone diseases, particularly osteoporosis, resulting from defective bone remodeling.

BACKGROUND OF THE INVENTION

Osteoporosis, a disease in which loss of bone mass causes skeletal deformities and fractures, affects nearly 20 million people, mostly women, in the United States alone. Development of new therapies for this disease has suffered from the absence of an appropriate animal model.

Osteoporosis has been defined as the clinically significant loss of bone mass without abnormality in either its composition or the proportion of its mineral and organic phases (1; see the appended Citations). Involutional (including postmenopausal and senile forms) and glucocorticoid therapy-induced osteoporosis are the two most frequent etiologies in developed countries. In the U.S. alone, the cost of treatment for osteoporosis-related fractures was estimated at 7–10 billion dollars in 1987 (2). It has been calculated that a person in the U.S. dies every 20 minutes as a result of complications from osteoporosis (3). The burden that osteoporosis places on society will inevitably grow as the number of elderly increases in coming decades. Treatment with estrogens and other agents can slow or prevent bone loss in women, (particularly if administered shortly after menopause; 4). However, effective, safe and well-tolerated therapy for established involutional osteoporosis has yet to be achieved (reviewed in 5,6). The development of new therapeutic approaches for osteoporosis would be facilitated by a better understanding of the disease pathogenesis, a goal that has been hindered by the lack of appropriate animal models.

Bone remodeling and the pathophysiology of osteoporosis. Bone remodeling is the ever-occurring skeletal process that is ultimately responsible for the development of acquired osteoporosis (7). Remodeling occurs at discrete sites scattered throughout the skeleton (7). The process is characterized by functional coupling of the activities of osteoclasts and osteoblasts (reviewed in 8). Thus, in skeletal balance, the mount of bone deposited by osteoblasts at a remodeling site is mirrored by the amount removed previously by osteoclasts. Regardless of cause, systemic osteoporosis always reflects circumstances in which osteoclast activity is enhanced relative to that of osteoblasts. Since bone deposition is generally initiated following bone resorption, one therapeutic strategy for osteoporosis has been to attempt a transient activation of osteoclasts in the hope that osteoblasts would subsequently deposit more bone than that removed by the osteoclasts. It follows conceptually that suppressed bone resorption might herald a reduced rate of bone remodeling and thus diminished bone formation. In fact, the most common form of involutional osteoporosis is characterized by slow remodeling in which bone formation is reduced more than is resorption (9).

Molecular and cellular mechanisms of bone remodeling. Bone resorption by osteoclasts occurs at a given bone remodeling site for only about 7–10 days (10). Murine models of osteoporosis have demonstrated that generation of osteoclasts from hematopoietic precursors is critically dependent on the production of macrophage-colony stimulating factor (M-CSF; 11), as well as the src gene product, (a protein-tyrosine kinase which osteoclasts express at high levels; 12,13). Many molecules which increase bone resorption by osteoclasts, (including interleukin-1, IL-1; tumor necrosis factors, TNF-$\alpha$ and -$\beta$; parathyroid hormone, PTH; and, 1,25-(OH)$_2$vitamin D$_3$[1,25-(OH)$_2$D$_3$], may act indirectly by activating secretion of factors from osteoblasts that, in turn, act on osteoclasts (14–16).

Candidate molecules for coupling bone resorption by osteoclasts to bone formation by osteoblasts include transforming growth factor-$\beta$ (TGF-$\beta$) and insulin-like growth factor-1 (IGF-1); both of which proteins a) are present in significant amounts in bone matrix and b) have been reported to enhance osteoblast activity (17,18). Once activated in vitro, osteoblasts appear to undergo a stereotypic sequence of proliferation, followed by increased production of alkaline phosphatase, followed finally by mineralization and production of bone matrix proteins such as osteocalcin and osteopontin (19,20). At a particular bone remodeling site, osteoblast activity and mineralization may require several months to reach completion (8). In addition to osteoblasts and osteoclasts, mononuclear phagocytes (M$\phi$) may briefly replace osteoclasts at a resorptive cavity surface in the remodeling site (21). Osteocalcin and other matrix proteins exposed by osteoclasts may act as chemoattractants for M$\phi$ and possibly other cell types (22). Mast cells may also be present in increased numbers at sites of bone remodeling, and especially in post-menopausal osteoporosis (23,24). Recently, mast cell-deficient W/W$^v$ mice have been reported to have alterations in the remodeling process (25) even though no skeletal abnormalities are evident. The defective gene product in the W/W$^v$ animals, c-kit, is a cell surface receptor for a cytokine encoded by the Sl locus (reviewed 26,27). Since the in vitro effects of the Sl cytokine are not limited to promoting mast cell growth, it seems that this cytokine might well exert its effects on remodeling by mechanisms that are independent of the mast cell-deficiency. In summary, the role that mast cells, M$\phi$, or other marrow cells, e.g., lymphocytes and fibroblasts, play in normal and osteoporotic bone remodeling remains uncertain.

IL-4 and its potential influence on bone remodeling and osteoporosis. IL-4 is a 15 kD glycoprotein produced by mast cells and T-lineage cells, especially mature CD4$^+$ T cells (28,29). IL-4 has pleiotropic effects on a wide variety of hematopoietic and other cell types, including abrablasts and endothelial cells (28–31). The intracellular signal transduction pathways by which IL-4 acts remain to be defined, but they appear to differ significantly from other pathways of cytokine signaling (32). To date, IgE production by B-lineage cells is the only normal function that has been reported to depend on the production of IL-4 in viva (33,34).

IL-4 transgenic mice. Three groups have reported generating IL-4 transgenic mice.

Tepper et al. (83) fused a genomic IL-4 coding region to immunoglobulin promoter and enhancer elements derived from mouse and human immunoglobulin heavy chain loci, respectively. The construct (termed Ig.IL4) was introduced into fertilized mouse oocytes, and the resultant overexpression of IL-4 in the transgenic mice reportedly induced a complex inflammatory reaction resembling that observed in certain human allergic disease. In addition, Burstein et al.

(83a) observed that IL-4 over-expression also had profound effects on the B cell function of these animals. The authors stated that the IL-4 transgenic animals are potentially powerful models for studying the initiation and control of inflammatory reactions depending upon Ag-specific IgE production. See also international patent publication No. WO 91/13979 (Leder et al.).

Müller et al. (83b) describes insertion of an IL-4-encoding construct into the mouse germ line under the control of the immunoglobulin heavy chain enhancer/promoter elements. In contrast to the IL-4 transgenic mice described by Tepper et al., the Müller et al. mice reportedly did not exhibit measurable alterations in the T cell compartment even though the level of transgene expression was sufficient to maintain Ia hyper-expression in B cells. The latter IL-4 transgenic mice thus reportedly provided an experimental model to test the effects of chronic Ia hyperexpression on B cells, and whether this is sufficient, per se, to lead to the development of autoimmune disease. No autoimmune disease was observed in the initial report (83b).

Lewis et al. (35) disclosed generation of transgenic mice in which increased IL-4 expression was selectively targeted to the thymus. The present FIG. 1 details the transgene expression construct (lck-IL-4). Three transgene-positive mice expressing detectable transgene-derived mRNA were obtained after microinjection of the lck-IL-4 construct into oocytes. The founder animals, designated #1315, #4453, and #4475, reportedly displayed a distinct perturbation in development of T-lineage cells.

SUMMARY OF THE INVENTION

We describe a disorder in bone remodeling in mice that inappropriately express the cytokine interleukin-4 (IL-4), the histological features of which are strikingly similar to those observed in cases of severe human involutional osteoporosis. These findings demonstrate that constitutive IL-4 expression in hematopoietic cells can have a dramatic negative influence on bone remodeling in vivo, and indicate that IL-4, itself, or an IL-4-induced pathway may contribute to the development of osteoporosis in humans. The exemplary lck-IL-4 mouse should serve as a useful model for the in vitro and in vivo evaluation of therapies for the prevention and treatment of osteoporosis as well as other defects in bone remodeling.

The invention provides such an in vivo assay for selecting a candidate therapeutic for treating diseases involving defective bone remodeling such as osteoporosis. A candidate reagent is administered to an IL-4 transgenic mammal, e.g., a mouse, whose cells contain a recombinant IL-4 coding sequence operably linked to a promoter sequence which is transcriptionally active in bone marrow cells. The promoter sequence is preferably transcriptionally active in lymphoid cells, particularly T cells. Representative promoters include the lck promoter and IL-2 promoter. At the time the candidate reagent is first administered, the IL-4 transgenic mammal is either symptomatic of, or asymptomatic of, an osteoporotic phenotype. The osteoporotic phenotype may be characterized by one or more symptoms selected from among histopathology showing reductions in cortical and trabecular bone mass, tetracycline bone labeling showing reduced osteoblast activity, and histomorphometric analysis showing a flattened appearance of osteoclasts and osteoblasts. The candidate reagent is selected as a candidate therapeutic for treating osteoporosis if either amelioration of, or delay in the onset of, the osteoporotic phenotype is observed following administration of the candidate reagent to the IL-4 transgenic mammal. In alternative embodiments, the candidate reagent may be administered to an animal symptomatic of an osteoporotic phenotype as a result of either adoptive transfer of IL-4 expressing cells into the animal or administration of IL-4 protein to the animal. The candidate reagent is preferably an antagonist of IL-4, such as an antibody against IL-4, an antibody against IL-4 receptor, or a soluble IL-4 receptor molecule. The antagonist of IL-4 may be directed against cell types, particularly T cells, which constitutively expresses IL-4.

The invention also provides an in vitro assay for selecting a candidate therapeutic for defects in bone remodeling. A candidate reagent is administered to a population of cells or tissue isolated from an IL-4 transgenic mammal whose cells contain a recombinant IL-4 coding sequence operably linked to a promoter sequence which is transcriptionally active in bone marrow cells. The isolated cells or tissue may be selected from among bone explants, lymphoid cells, T cells, bone marrow cells, osteoblasts, and osteoclasts. The candidate reagent is selected as a candidate therapeutic for treating defects in bone remodeling if either amelioration of, or delay in the onset of, an osteoporotic cell phenotype is observed following administration of the candidate reagent to the isolated cells or tissue. The osteoporotic cell phenotype may be characterized by one or more properties selected from among decreased osteoblast or osteoclast cell growth, decreased osteoblast or osteoclast metabolic activity, and histomorphometric analysis showing a flattened appearance of osteoblasts or osteoclasts.

DETAILED DESCRIPTION OF THE PREFERRED EMBODIMENT

Figure 1:
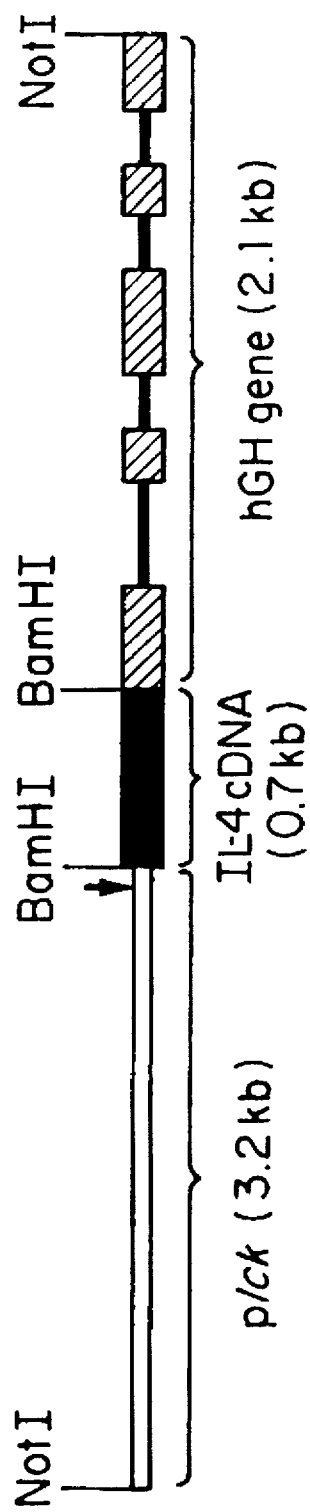
FIG. 1 (Prior Art) is a map of the lck-IL-4 transgene construct, as described in Example 1.

To study the effects of IL-4 in vivo, we generated transgenic mice in which an IL-4 cDNA is expressed under the control of the proximal lck promoter (35,36). The lck gene encodes a protein-tyrosine kinase principally expressed by T-lineage lymphocytes and NK cells (37–39). Our original intent in generating lck-IL-4 mice was to determine the effect of increased intrathymic expression of IL-4, since IL-4 has been proposed to have a possible physiologic role in thymic development (40–42). We chose to use the proximal promoter segment of the lck gone to drive IL-4 expression, since its transcriptional activity in the context of the normal lck gone is approximately 50–100-fold higher in thymocytes than in peripheral T cells (36,43). This pattern of increased expression in T cells was also true for the lck-IL-4 transgene in mice of the initial founder #1315 inbred line of animals. The latter mice also consistently exhibited multiple perturbations of T-lineage development that we have shown are due to increased IL-4 secretion (35). Remarkably, we found that lck-IL-4 mice, by 3 to 4 months of age, also develop severe progressive osteoporosis that closely resembles the human involutional osteoporosis. This previously unpublished observation forms the basis of the present disclosure.

As discussed below in Examples 3–6, the #1315 line of lck-IL-4 transgenic mice have a genetic bone disease characterized by bone loss that is grossly evident by an abnormal translucent appearance of the skeleton, which is especially well seen in the ribs. With aging, many lck-IL-4 mice also develop gross kyphosis of the thoracic spine, a feature which is conveniently confirmed radiographically. No fractures of the vertebral bodies or of other bones have been found. Microradiography invariably demonstrates significant losses of cortical and trabecular bone mass throughout the skeleton. This bone disease radiographically and histopathologically closely resembles severe osteoporosis which occurs in humans. The stigmata of other bone diseases, such as osteomalacia, renal osteodystrophy, or primary hyperparathyroidism, are absent. Serum chemistries also argue against a primary metabolic or endocrine disorder mediating bone disease in these mice. Lower serum alkaline phosphatase and osteocalcin levels in lck-IL-4 mice compared to controls are consistent with the histopathologic studies, which indicate that osteoblast activity is markedly reduced in these animals. Histomorphometric studies confirm that lck-IL-4 mice have striking reductions in both cortical and trabecular bone mass. In vivo tetracycline bone labeling studies confirm that reduced osteoblast activity is the major factor leading to osteoporosis. In toto, the characteristics of the bone disease in these IL-4 transgenic animals are virtually indistinguishable from those in the low turnover form (Type II) of human osteoporosis.

The osteoporotic disease in lck-IL-4 mice is of similar severity in both sexes, and has remained phenotypically stable during propagation of one lck-IL-4 inbred animal line, from founder #1315, for more than eight generations on a C57BL/6 genetic background. Importantly, histomorphometric analysis of the bone tissue from an independently derived lck-IL-4 founder animal, #4475, in which the transgene has presumably integrated at a different site than for #1315, also demonstrates severe bone loss and decreased osteoblast-lineage function as compared to an age-matched control animal. This indicates that the bone disease phenotype observed in lck-IL-4 mice is mediated by transgene-derived IL-4, rather than by a perturbation of an endogenous gene as a result of transgene integration. Further evidence that expression of IL-4 mediates the observed bone disease comes from an analysis of other transgenic mice we have generated using a pIL-2/IL-4 construct. This construct is similar to the lck-IL-4 construct except that a human IL-2 promoter segment has been inserted in place of the proximal lck promoter segment. Histomorphometric analysis shows that pIL-2/IL-4 mice consistently have decreased bone mass compared to littermate controls, indicative of osteoporosis. The degree of osteoporosis in pIL-2/IL-4 mice is less than in lck-IL-4, consistent with the lower overall activity of the IL-2 promoter, compared to the proximal lck promoter. Taken together, these findings show that expression of IL-4 in vivo in certain contexts can induce a form of osteoporotic bone disease.

Although it remains to be shown that increased IL-4 secretion, particularly within the bone microenvironment, is responsible for the osteoporosis phenotype of the #1315 line, our preliminary data showing increased IL-4 mRNA in transgenic bone marrow is consistent with this possibility. Bioassays for IL-4 indicate that bone marrow cells from transgenic mice do not produce IL-4 in pharmacologic amounts. Taken together, the findings indicate that the #1315 line of lck-IL-4 transgenic mice is a useful model for studying the pathogenesis of osteoporosis.

Significance of the lck-IL-4 mouse model. Information potentially relevant to the pathogenesis of osteoporosis has been obtained previously in studies using tissue explants or cell lines cultured in vitro, but a major limitation has been the lack of a convenient model for extrapolating these results to the in vivo situation. Reported in vivo models of osteoporosis have required hormonal or pharmacologic manipulations to achieve osteopenia (64–66). Further, unlike lck-IL-4 mice, which consistently develop severe kyphosis associated with generalized osteoporosis, many of these models do not yield such osteopenic sequelae. A mouse strain with an uncharacterized genetic predisposition for osteopenia has been reported (67), but it is not clear that this strain develops significant bone disease. Defining the mechanisms that lead to osteoporosis in our model, which is histologically and phenotypically remarkably similar to the most common form of the human disease, should provide general insights into the pathogenesis of osteoporotic disorders. Most importantly, this model may afford insights into designing new forms of treatment for osteoporosis and may be a useful tool for evaluating candidate drugs. Since trials of systemic IL-4 treatment for neoplasms are already underway (68), the subject animals and cells should also provide information as to the potential effects of IL-4 in vivo, and could have practical implications for understanding risks and benefits of cytokine immunotherapy.

Selection of candidate therapeutics for treating osteoporosis. The invention provides an in vivo assay for selecting a candidate therapeutic for treating osteoporosis. A candidate reagent is administered to an IL-4 transgenic mammal whose cells contain a recombinant IL-4 coding sequence operably linked to a promoter sequence which is transcriptionally active in lymphoid and preferably bone marrow cells. At the time the candidate reagent is first administered the IL-4 transgenic mammal may be either symptomatic of, or asymptomatic of, an osteoporotic phenotype. The candidate reagent is selected as a candidate therapeutic for treating osteoporosis if either amelioration of, or delay in the onset of, the osteoporotic phenotype is observed following administration of the candidate reagent to the IL-4 transgenic mammal.

The IL-4 transgenic mammal is preferably a mouse but may alternatively be any mammal including rats. Transgenic refers to an animal that is genetically recombinant in all its cells by virtue of the introduction of a nucleic acid into the germ line. The subject nucleic acid can be introduced into the germ line by transduction or transfection using known procedures, such as described below for the representative lck-IL-4 transgenic animals.

The cells of the IL-4 transgenic mammal contain a recombinant IL-4 coding sequence operably linked to a promoter sequence which is transcriptionally active in lymphoid and preferably bone marrow cells. IL-4 coding sequences are known in the art; see, for example, U.S. Pat. No. 5,017,691 (Lee et al.), which is incorporated by reference herein. Representative promoter sequences which are transcriptionaly active in bone marrow cells include the proximal lck promoter, IL-2 promoter, and ost promoter (68a). Proximal lck promoter refers to the region from −584 to +37 with respect to the transcription start site of the lck gene (which encodes a lymphocyte-specific membrane-associated protein tyrosine kinase, p56$^{lck}$, that is a member of the src gene family and participates in T-lymphocyte signaling in mammals).

Representative candidate reagents for the subject assay include IL-4 antagonists which are capable of blocking the normal IL-4/IL-4 receptor interaction, and include, for example, IL-4 specific antibodies, IL-4 receptor specific antibodies, IL-4 receptor polypeptides, and binding fragments thereof. IL-4 specific antibodies are available from commercial sources, such as ICN Biomedicals (Irving, Calif.) and are disclosed in U.S. Pat. Nos. 5,031,824 (Abrams et al.) and No. 5,041,381 (Abrams et al.), which are incorporated by reference herein. See also international patent publications No. WO 91/09059 (Ramanathan et al.) and No. WO 89/06975 (Coffman et al.). IL-4 receptor specific antibodies are disclosed in international patent publication No. WO 89/09621 (Ritter et al.). Soluble IL-4 receptors are disclosed in international patent publications No. WO 90/05183 (Cosman et al.) and No. WO 90/03555 (Galizzi et al.).

A second class of representative candidate reagents and procedures are targeted to cells, such as T cells, that constitutively express inappropriate amounts of IL-4. These include cell-lineage specific monoclonal antibodies (or antigen-binding sites thereof, whether made by hybridoma or recombinant techniques), such as anti-CD4, anti-CD8, anti-Thy-1, and anti-NK1-1 monoclonal antibodies, either unconjugated or conjugated to immunotoxins, as well as procedures such as thymectomy and bone marrow transplantation.

The candidate reagent is typically administered by injection, e.g., intravenously, intraperitoneally, subcutaneously, intradermally, or intraosteously.

At the time the candidate reagent is first administered, the IL-4 transgenic mammal is either symptomatic of an osteoporotic phenotype or asymptomatic of an osteoporotic phenotype. This permits selection of candidate therapeutics for treating osteoporosis in terms of ameliorating the osteoporotic phenotype and/or delaying the onset of the osteoporotic phenotype, respectively. The osteoporotic phenotype is characterized by one or more findings or symptoms selected from among the following Group 1, or two or more findings selected from Group 2. Group 1 osteoporotic findings include: a) histopathology showing reductions in both cortical and trabecular bone mass; b) in vivo tetracycline bone labeling showing reduced osteoblast activity in deposition of calcium carbonate (hydroxyapatite) and mineralization into bone; and c) histomorphometric analysis showing a flattened appearance of osteoclasts and osteoblasts, as described in Example 4. Group 2 osteoporotic findings include: a) bone loss evident as an abnormal translucent appearance of the skeleton; b) kyphosis of the thoracic spine confirmed by radiographic examination especially in lateral views of the spine; c) loss of trabecular and cortical bone mass throughout the skeleton, grossly evident on dissection as bones with an abnormal, semitranslucent appearance and a consistency similar to cartilage rather than healthy bone; and d) increased general bone fragility with the absence of stigmata of other bone diseases (e.g., osteomalacia, renal osteodystrophy, and primary hyperthyroidism), and the absence in the serum chemistry of a primary metabolic or endocrine disease, but with lowered serum alkaline phosphatase and osteocalcin levels.

The candidate reagent is selected as a candidate therapeutic for treating osteoporosis if either amelioration of, or delay in the onset of, the osteoporotic phenotype is observed following administration of the candidate reagent to the IL-4 transgenic mammal, as compared to control IL-4 trangenic mammals.

In vitro assays. The invention also provides in vitro assays for selecting therapeutic agents for treating osteoporosis. In this case the candidate reagent is added, e.g., at a concentration of approximately 1 pM to 1 mM, to a culture of test cells or tissue (e.g., bone explants, lymphoid cells, T cells, bone marrow cells, osteoblasts, and/or osteoclasts) isolated from the subject IL-4 transgenic mammal. The test cells are isolated when the IL-4 transgenic mammal is either symptomatic of, or asymptomatic of, the osteoporotic phenotype.

The test cell population(s) may alternatively be isolated from mammals that possess a bone marrow altered by experimental manipulations, e.g., animals subjected to lethal irradiation and bone marrow reconstitution with enriched populations of IL-4 producing cells. The test cells, themselves, may also be genetically engineered with an IL-4 construct. In an alternative embodiment, test cells may be isolated from mammals that have been genetically engineered to decrease the level of IL-4 expression in lymphoid tissues and bone marrow.

The in vivo assay provides a preliminary screen for candidate reagents which ameliorate or delay an osteoporotic cell phenotype, as indicated by: a) decreased osteoblast or osteoclast cell growth (e.g., as measured by tritiated thymidine incorporation in vitro in cultures containing optimal concentrations of growth factors); b) decreased osteoblast or osteoclast metabolic activity (e.g., for osteoblasts synthesis of alkaline phosphatase, secretion of tetracycline-labeled calcium phosphate, and the like; for osteoclasts synthesis of TRAP, and formation of pits in bone slices, and the like); and/or c) an abnormal flattened cell shape observed in histological cross-sections of cells grown in vitro on an appropriate extracellular matrix.

The invention also provides a method of transferring an osteoporotic phenotype from an IL-4 transgenic mammal to a syngenic recipient mammal, by transferring cells such as bone marrow, stromal, lymphoid, and/or T cells into the recipient. Such cell transfers are conveniently conducted by transplantation of isolated cell suspensions, tissue samples, and the like. The transfer of cell suspensions may be made by injection, e.g., intravenous, intraperitoneal, intradermal, subcutaneous, or intraosseous instillation of cells. A suitable number of cells will depend upon the size of the mammal, for example, approximately $10^4$ to $10^7$ cells per mouse and larger numbers of cells for larger animals.

Directed manipulation of bone remodeling. The invention also provides assays for selecting candidate therapeutic agents for altering bone remodeling in a mammalian host. By alterating bone remodeling is meant qualitative or quantitative inhibition or enhancement of either a normal or diseased bone remodeling process that is ongoing in an animal or patient. The alteration of bone remodeling may include changes in rate, extent, or amount of mineralization, percentage of bone mass attributable to trabecular versus cortical bone, the osteoblastic amount of collagen, and the like. Bone diseases in which altering bone remodeling may be useful include osteoporosis, osteopetrosis, non-union fractures, formation of bony spurs (e.g., at tendon insertion sites), Paget's disease, and the like. In bone disease such as osteoporosis or osteopetrosis it may be useful to treat the disease in a stepwise fashion, first with an agent selected to interrupt the ongoing remodeling process by stimulating an osteoporotic phenotype with an IL-4 bone therapy, and then with an agent selected to reverse the IL-4 osteoporotic phenotype.

In the subject IL-4 bone therapy, an IL-4 agent is introduced into a subject in an amount and for a time sufficient to alter bone remodeling. The IL-4 agent may be an IL-4 polypeptide (e.g., introduced systemically by intravenous injection or infusion, or infused into a bone cavity through a surgically implanted bone catheter, or injected locally at the bone remodeling site). Alternatively, the IL-4 agent used in the IL-4 bone therapy may take the form of genetically engineered cells, e.g., fibroblasts or other cell types expressing a recombinant IL-4 polypeptide, in which case the IL-4 expressing cells are adoptively transferred into the animal or patient. The IL-4 agent used in the IL-4 bone therapy may alternatively be a gene transfer vector, e.g., a retroviral vector capable of infecting and inducing IL-4 expression in cells at a the treatment site.

In situations where the bone disease involves a non-union fracture, bony spur, or a cosmetic bony defect (e.g., resorption of supernumerary digits, or facial reconstruction), a similar stepwise approach is advised, i.e., IL-4 bone therapy followed by treating with an agent to reverse the IL-4 osteoporotic phenotype, followed by treating with an agent to induce ossification. For example, following surgical intervention to re-establish a mechanical union (e.g., by plastic surgery), it may prove highly effective to start treatment with an IL-4 bone therapy that stimulates altered bone remodeling in the surgical area. In this manner any bone defects are corrected and the site is prepared for ossification. As a next step, the altered bone remodeling may be stopped (i.e., by treating with an agent reversing an IL-4 osteoporotic phenotype or by discontinuing the IL-4 administration), and then ossification may be induced by administering a bone osteogenic growth factor or factor stimulating mineralization and/or cortical bone formation. By ossification is meant mineralization of bone (e.g., as measured using $^{45}$Ca incorporation or incorporation of tetracycline), formation of an increased mass of cortical bone (e.g., the mass of cortical bone compared with trabecular bone), and the like.

A variety of IL-4 treatments are available for stimulating bone remodeling with IL-4 bone therapy. For example, controlled release formulations containing an IL-4 agent (i.e., IL-4 polypeptide, recombinant cells, or vectors, as described above) may be implanted during surgical intervention at a bone site. Illustrative examples of such controlled release materials include biocompatible sponges (e.g., fibrillar collagen-heparin surgical sponges and the like), capsules (e.g., made of alginates, gelatin, and the like), gels (e.g., collagen, hyaluronate), and the like. Those skilled in the art will recognize that pharmacological properties and biological activities of an IL-4 agent in blood may not model the properties and activities in bone, and that local modeling may be required to determine the optimal conditions for IL-4 bone therapy.

The assays disclosed herein provide in vitro and in vivo models that are useful in determining pharmacological dosage ranges, timing, rates for administration, and delivery methods for IL-4 bone therapy. In one example, a 1 mm defect is created in the distal region of the femur of a mouse and after a period of healing transgenic murine cells expressing recombinant IL-4 (e.g., cells from an IL-4 transgenic animal) are injected into the defect site. The transferred cells stimulate altered bone remodeling at the site, and may promote the rate at which bone reunion occurs in the presence (or absence) of bone growth factors (e.g., TGF-β, IGF-1, IGF-2, bone morphogenetic proteins, osteogenein, and osteocalcin).

Those skilled in the art will recognize that candidate therapeutic agents that are selected in the assays of the invention as agonists or antagonists of an osteoporotic phenotype may prove useful in their own right as therapeutic agents for promoting ossification in bone. Alternatively, the candidate therapeutics may prove useful in a stepwise bone therapy protocol. For example, after disrupting an ongoing diseased bone process with an IL-4 bone therapy, treatment may next be initiated with a candidate therapeutic agent designed to reverse an IL-4 osteoporotic phenotype. In the murine femoral bone model described above, a candidate therapeutic agent may be tested for its ability to promote the rate of reunion and ossification.

The invention is further illustrated by the following representative examples.

EXAMPLE 1

Preparation of the lck-IL-4 construct

The lck-IL-4 construct (FIG. 1) was produced by inserting a full-length 0.7-kb murine IL-4 cDNA BamHI fragment (69) into the calf intestinal phosphatase-treated BamHI site of an expression vector, p1017 (70), using standard subcloning techniques (71). In the final construct, the murine IL-4 cDNA segment was located 3' to a 3.2-kb murine proximal lck promoter segment at +37 with respect to the transcription start site (36), and 5' to a 2.1-kb BamHI-EcoRI fragment of the human growth hormone (hGH) gene (72). Referring to FIG. 1, the transcription start site of the proximal lck promoter is indicated by an arrow, the IL-4 cDNA segment is indicated by the solid rectangle, and hGH exon sequences are indicated by crosshatching. The IL-4 segment was embedded within the hGH gene since intronic sequences appear to be required for efficient transgene expression; the basis for this requirement remains poorly understood (73). Of course, one concern would be that hGH is being produced by the construct in biologically significant amounts in these mice. However, positioning the cDNA 5' to the translation initiation codon of the hGH gene results in undetectable serum levels of human growth hormone (<50 picograms/ml by RIA) in mice bearing the lck-IL-4 construct, or in other lines of mice bearing similarly constructed transgenes containing the 3' hGH gene segment (43,70; and data not shown).

EXAMPLE 2

Generation of lck/IL-4 transgenic mice

A 6.0-kb NotI fragment containing the lck-IL-4 construct was purified by agarose gel electrophoresis onto DEAE-nitrocellulose paper (71) and diluted to 2 ng/ml in 10 mM Tris-Cl, 0.1 mM EDTA, pH 7.5. Aliquots of this preparation were micro-injected into the pronuclei of C57BL/6J X DBA/2J F$_2$ hybrid mouse zygotes. The micro-injected embryos were transferred to oviducts of anesthetized C57BL/6 pseudopregnant females using standard techniques (74). Mice born to these pseudopregnant females were analyzed for transgene integration at 2–3 weeks of age by hybridizing blotted tail DNA with a hGH fragment probe (72). Three lck-IL-4-positive founder mice expressed detectable transgene-derived mRNA in thymic tissue (35; and unpublished data). These founder animals, designated #1315, #1453, and #4475 displayed a distinct perturbation of T-lineage cell development which included thymic hypoplasia and the absence of peripheral CD8$^+$ T cells (35). The estimated number of copies of the lck-IL-4 transgene in the #1315, #4453, and #4475 founders was 8,5, and 5, respectively, based on densitometry of tail DNA blots hybridized with a 0.6-kb IL-4 cDNA probe (data not shown). Since the transgene copy number and the degree of perturbation of T-lineage cells in these three founders were similar, this indicated that the particular integration site of the transgene did not have a significant influence on the T-lineage cell phenotype we observed. The #1315 founder and its progeny were bred with C57BL/6 mice to maintain this line and permit a more detailed characterization of these lymphocytic perturbations. Treatment of #1315 line mice with anti-IL-4 monoclonal antibody clearly demonstrated that the perturbations of T-lineage cells in these mice was dependent on the secretion of IL-4 and was not due to disruption of an endogenous gene as a result of transgene integration (35).

EXAMPLE 3

Radio graphic abnormalities in the #1315 line of lck-IL-4 mice

Figure 2:
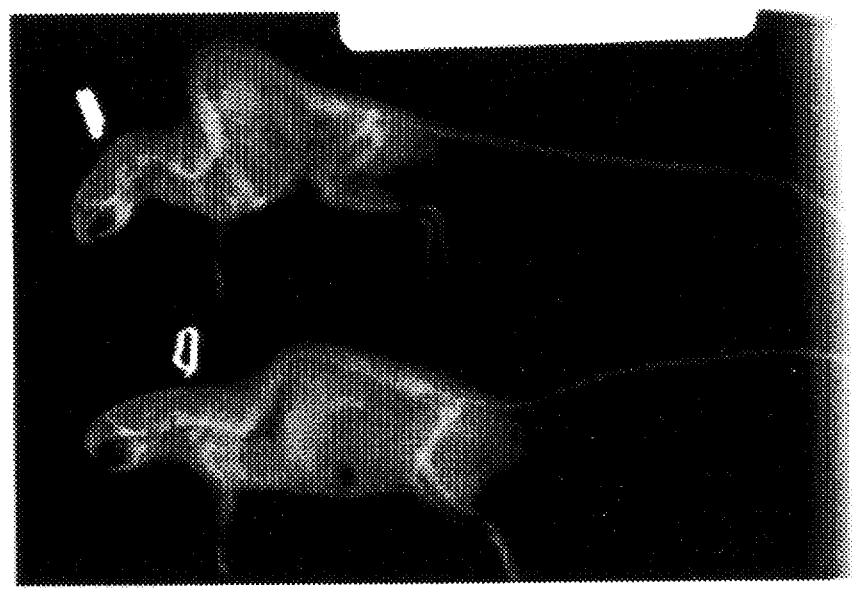
FIG. 2 presents lateral X-ray views showing gross kyphosis of a trangenic mouse (upper view) compared to a nontransgenic littermate control (lower view), as described in Example 3.

The #1315 male founder was sacrificed at 7 weeks of age after it had successfully bred with a normal C57BL/6 female. A translucent appearance of the founder animal's ribs was noted at this time. By 12 weeks of age, a kyphotic posture was evident in all transgenic progeny of this founder. Conventional radiographs which included lateral spine views confirmed severe kyphosis of the spinal column of the transgenic progeny (FIG. 2, upper view), as compared with nontransgenic littermate controls (FIG. 2, lower view). No wedging of vertebral bodies suggestive of compression fractures was evident. During dissection of six-week-old lck-IL-4 mice which had been sacrificed to obtain tissues for analysis, we also observed that their bones had a "washed-out" appearance and were much easier to cut than bones of littermate controls, suggesting that lck-IL-4 mice had a significant generalized reduction in bone mass. These phenotypic abnormalities have remained consistent after more than 9 generations of backcrossing the #1315 line with normal C57BL/6 mice, and have been of similar severity in males and females. The bone disease in lck-IL-4 mice did not appear to be due to a nutritional deficiency. The weight of transgenic and nontransgenic littermates prior to 12 weeks of age was similar even though marked decreases in bone mass were already evident. After the onset of severe kyphosis, the weight of transgenic animals begins to decline compared to nontransgenic littermates. This probably reflects a decreased caloric intake due to their limited mobility. Severely kyphotic mice have been euthanized at this point to prevent suffering.

Although lck-IL-4 mice had generalized bone fragility and progressive kyphosis, they were otherwise free of dysmorphic features, suggesting their major disease process was osteoporosis. To evaluate in detail the entire skeleton for evidence of osteoporosis or other abnormalities, microradiography was performed. To allow optimal studies, lck-IL-4 and littermate control mice were first euthanized and then fixed in 10% neutral formalin prior to radiography. Representative results are shown in Table 1. Lck-IL-4 mice had a generalized decrease in cortical and trabecular bone mass, which was particularly evident in the long bones and vertebrae, respectively.

Table 1. Cortical thickness and percent cortical area bone indices of 3-month-old lck-IL-4 (n=4) and nontransgenic littermate control (n=4) mice. Shown are mean values±standard error of means. Statistical significance was calculated using the unpaired two-tailed Student's t test comparing the lck-IL-4 and littermate control means.

|  | lck-IL-4 | Littermate control | Statistics |
|---|---|---|---|
| Mid-radius |  |  |  |
| Cortical thickness (mm) | 0.20 ± 0.01 | 0.29 ± 0.01 | P < 0.0001 |
| Percent cortical area | 52.6 ± 1.3 | 71.3 ± 1.3 | P < 0.00002 |
| Mid-ulna |  |  |  |
| Cortical thickness (mm) | 0.35 ± 0.02 | 0.52 ± 0.05 | P < 0.02 |
| Percent cortical area | 68.0 ± 2.3 | 83.8 ± 1.5 | P < 0.002 |

Microradiography documented marked and generalized reductions in cortical and trabecular bone mass in lck-IL-4 mice compared to littermate controls (FIG. 2). Our microradiographic analysis focused on the long bones, since these are particularly useful for quantifying bone mass by calculating cortical bone indices (74a). By these criteria lck-IL-4 mice consistently had markedly reduced total cortical bone thickness, area, and area as a percent of total bone volume compared to littermate controls (Table 1 and FIG. 3).

Figure 3A:
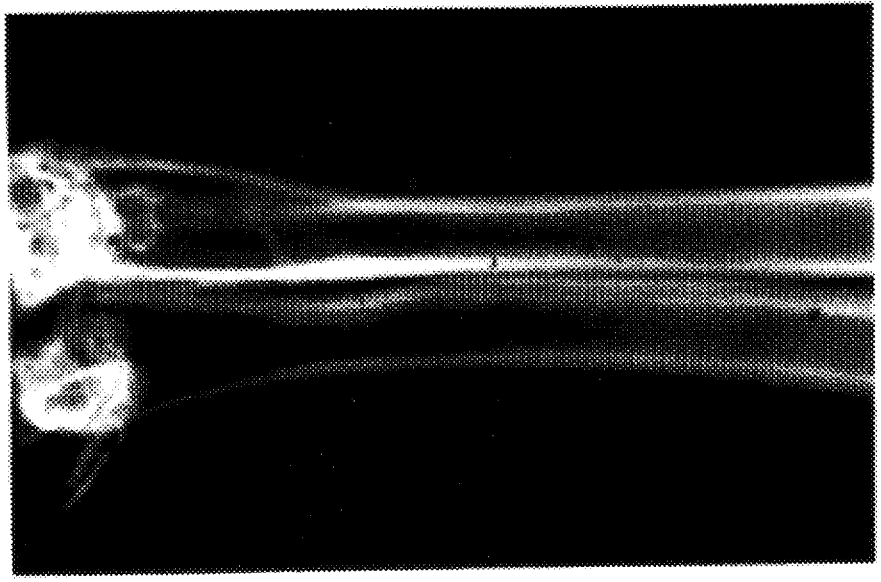
FIG. 3 shows skeletal radiography of lck-IL-4 and littermate control mice, as described in Example 3.
Figure 3B:
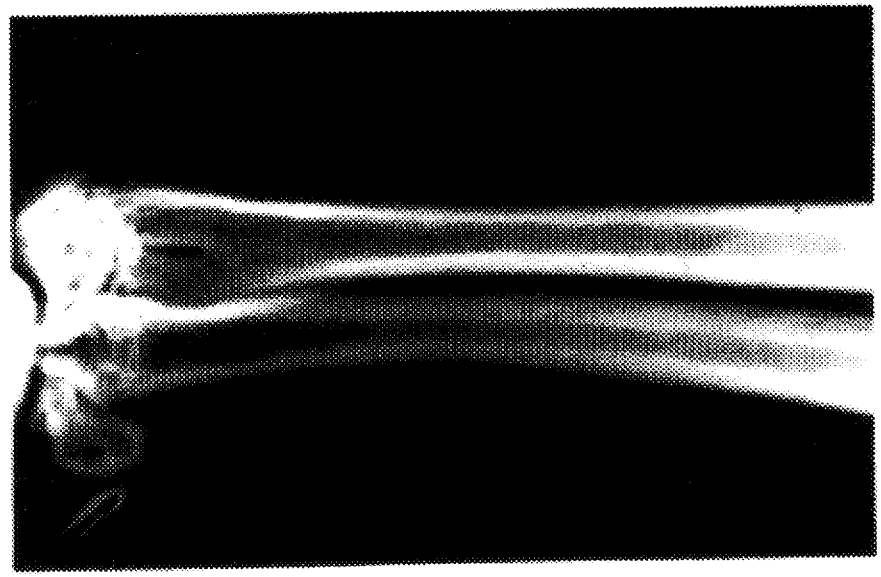
Figure 4A:
FIG. 4 shows alkaline phosphatase and tartrate-resistant acid phosphatase (TRAP) activity of bone tissue from lck-IL-4 and littermate control mice, as described in Example 4.
Figure 4B:
Figure 4C:
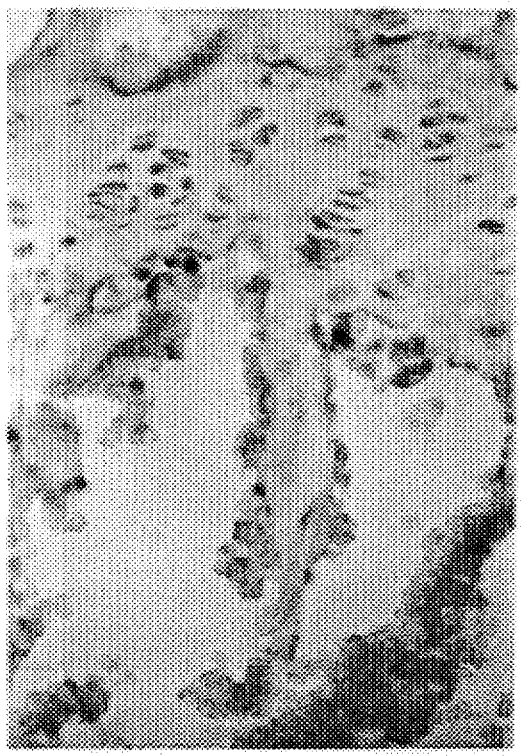
Figure 4D:

FIGS. 3A and 3B show lateral survey microradiographs, at identical magnification, of the forelimb of a three-month-old male lck-IL-4 mouse (3A) and a three-month-old non-transgenic male littermate (3B). Marked cortical thinning of the radius and ulna are evident in the transgenic mouse compared with the littermate control.

Importantly, no stigmata typical of endocrine or metabolic bone diseases, such as osteomalacia, renal osteodystrophy, primary hyperparathyroidism, or of congenital dysmorphic syndromes involving the skeleton were observed, indicating that these mice had an osteoporotic disorder.

EXAMPLE 4

Histopathology and histomorphometry of bone in lck-IL-4 mice

Since osteoporosis by definition requires the absence of abnormalities in the composition or the proportion of the matrix and mineral bone components, bone tissue from lck-IL-4 and nontransgenic littermates was examined histologically to exclude these perturbations. By light microscopy, decreased cortical and trabecular bone mass in tissue from transgenic animals was evident in vertebral bodies as well as in long bones. In accord with microradiographic results, trabecular bone volumes were decreased and the complexity of the trabecular network appeared reduced, a typical finding in severe involutional osteoporosis in humans (74b). At higher magnification of lck-IL-4 bone tissue, a particularly dramatic reduction in the number and cell height of osteoblasts lining trabeculae was found, suggesting that these osteoblasts were largely inactive. Again, in agreement with the radiographic studies, no signs of osteomalacia, hyperparathyroidism, or skeletal dysplasia were evident.

Although a mast cell-mediated mechanism for osteoporosis in lck-IL-4 mice is plausible, given that systemic mastocytosis can result in generalized osteoporosis (60,61), and IL-4 is a well-characterized mast cell growth factor in vitro (59), there were no significant differences between transgenic and nontransgenic animals in the number of mast cells in decalcified bone sections stained by toluidine blue. Furthermore, the number and appearance of mast cells in bone tissue or in bone marrow of lck-IL-4 and littermate control mice was similar after staining with either hematoxylin and eosin or with Giemsa, which enhances the detection of these cells (data not shown). As reported previously, we also failed to find increased numbers of mast cells at any soft tissue sites, including the skin and mucosal areas in lck-IL-4 mice (35). Taken together, these initial histologic studies suggested that markedly reduced osteoblast activity was likely to be an important mechanism for the development of osteoporotic bone disease in the #1315 line of lck-IL-4 mice. Although not conclusive, these studies also suggested that this bone disease was unlikely to be mediated by mast cells and was not accompanied by an increased rate of bone turnover.

To more precisely quantitate differences in bone volume between transgenic and control animals, sections from the third caudal vertebrae were histomorphometrically analyzed for trabecular bone volume (the percent of marrow space occupied by bone matrix expressed as the "percent total osteoblastic surface") and mean cortical width using standard light microscopic techniques (75). All samples were coded prior to their analysis. Histomorphometric analysis revealed significant decreases in total bone volume, total surface osteoid, and osteoblast surface area in bone tissue of lck-IL-4 mice (Table 3). Importantly, histomorphometric analysis of the bone tissue of an independently-derived lck-IL-4 founder animal, #4475, in which the transgene had presumably integrated at a different site than for the #1315 line, also demonstrated severe bone loss and decreased osteoblast-lineage function as compared to an age-matched control animal. This strongly indicated that the bone disease phenotype observed in lck-IL-4 mice was directly mediated by the transgene, rather than reflecting the perturbation of an endogenous gone as a remit of transgene integration.

To further document that osteoblast activity was depressed in lck-IL-4 mice, osteoblast function was assessed by determining the incorporation of tetracycline into osteoid matrix after intraperitoneal injection (75a). Bone tissue from transgenic mice clearly had reduced incorporation of this label compared to littermate control cells (Table 2) indicating that the formation of mineralizing bone was reduced in lck-IL-4 animals.

Table 2. Histomorphometric analysis of osteoblast activity in bone tissue of lck-IL-4 and or wild-type control mice. Mean values±the standard error of the mean are shown for the #1315 line and nontransgenic littermates.

|  | Age | Total Osteoblast Surface (%) | Total Tetracycline Surface (%) |
| --- | --- | --- | --- |
| lck-IL-4 #1315 line (n = 3) | 4 months | 10.6 ± 2.4* | 20.9 ± 2.2† |
| Nontransgenic littermates (n = 3) | 4 months | 18.0 ± 1.1 | 48.4 ± 10.2 |
| lck-IL-4 #4475 female founder | 9 months | 5.4 | ND |
| Control# | 9 months | 13.6 | ND |

*p < 0.05 compared with an age- and sex-matched C57BL/6 mouse.
†p < 0.03 compared with an age- and sex-matched C57BL/6 mouse.
An age- and sex-matched C57BL/6 mouse was used as a control.
ND = Not Determined Enzymo-histologic staining of bone sections for alkaline phosphatase (AP), an enzyme produced by osteoblasts, and for tartrate-resistant acid phosphatase (TRAP), an osteoclast-specific enzyme, provided additional insight into the bone disorder in lck-IL-4 mice. In transgenic bone tissue, AP activity associated with osteocytes or with osteoblasts lining the periosteum, endosteum, and trabeculae was markedly reduced as was TRAP activity associated with osteoclasts (FIG. 4). Histomorphometric analysis of TRAP-stained bone tissue also revealed that lck-IL-4 mice had consistent reductions in the numbers of resident osteoclasts compared to nontransgenic littermates. Together, these findings indicated reduced function of osteoblasts as well as osteoclasts in lck-IL-4 bone tissue.

For the enzymo-histological staining, bone tissue was fixed in 70% ethanol at 5° C. for 8–12 hrs, embedded in OCT freezing medium, and snap-frozen in liquid nitrogen-cooled isopentane. Sections were cut with a cryostat, collected onto Vectabone-treated glass slides, air-dried, and used immediately or stored at −70° C. Staining for alkaline phosphatase and tartrate-resistant acid phosphatase (TRAP) activities employed standard procedures [C. Liu et al., Histochem. 86:559, 1987]. For alkaline phosphatase detection, sections were incubated with a mixture of naphthol ASTR phosphate and the coupling azo dye, Fast Blue BB, in Tris-Cl buffer, pH 9.0 for 30 min at 37° C., and then rinsed thoroughly with distilled water. For TRAP activity, sections were incubated with naphthol ASTR phosphate with hexazotized parasoaniline in the presence of 10 mM tartrate in acetate buffer, pH 5.0 at 37° C. for 1 hr and then thoroughly rinsed with distilled water.

FIG. 4 shows enzymo-histologic staining of bone tissue from lck-IL-4 and littermate control mice. Alkaline phosphatase activity (blue staining) of frozen sections of tibiae (10×) from a two-month-old female lck-IL-4 mouse (FIG. 4A) is compared with a nontransgenic littermate control (FIG. 4B). In lck-IL-4 tissue there is a dramatic generalized reduction in alkaline phosphatase activity associated with osteoblasts lining the trabeculae, periosteum, and endosteum. Thinning of the cortical bone is also evident in the transgenic sample. Tartrate-resistant acid phosphatase (TRAP) activities (red staining) of metaphyseal regions of tibiae (40×) from the same mice are shown in FIGS. 4C (transgenic) and 4D (control), respectively. The intensity of staining is reduced in osteoclasts in lck-IL-4 tissue compared to that in the littermate control.

EXAMPLE 5

Serum chemistry studies

Serum chemistry and enzyme studies also argued against hyperparathyroidism, vitamin D deficiency, or renal insufficiency as the etiology for the generalized bone disease of lck-IL-4 mice (Table 3).

Table 3. Serum biochemistries in 9-week-old lck-IL-4 (n=5) and littermate control (n=3) mice. Transgenic and littermate control sera were analyzed in parallel for serum calcium, phosphorus, creatinine, and alkaline phosphatase activity (10 μl/test) using a Kodak EktaChem700XR Analyzer. Serum osteocalcin was determined using a commercial radioimmunoassay kit (Biomedical Technologies, Sloughton, Mass.) following the manufacturers instructions. Shown are mean values±the standard error of the mean.

|  | $Ca^{2+}$ (mg/dL) | Phosphorus (mg/dL) | Alkaline phosphatase (U/ml) | Creatinine (mg/dL) | osteocalcin (ng/ml) |
| --- | --- | --- | --- | --- | --- |
| lck-IL-4 | 10.0 ± 0.1 | 9.2 ± 0.3* | 113 ± 8* | 0.1 ± 0.0 | 84 ± 55* |
| littermate control | 10.2 ± 0.2 | 8.1 ± 0.5 | 176 ± 8 | 0.1 ± 0.0 | 162 ± 12 |

*p < 0.05 compared with LM control using the two-tailed Student's t test.

Transgenic and littermate-control animals had similar total serum calcium and protein levels (data not shown), indicating that serum free calcium levels were probably normal in lck/IL-4 mice. Lck-IL-4 sera exhibited a small but significantly increased phosphorus concentration. The normal serum creatinine (Table 3) and normal microscopic renal histology in lck-IL-4 mice (data not shown) argued against a renal disorder in phosphate clearance being responsible for this very modest hyperphosphatemia. The high-normal level of phosphorus also essentially excluded a primary hyperparathyroid disorder in lck-IL-4 mice, since abnormally increased parathyroid hormone secretion typically lowers serum phosphate levels by increasing renal phosphate clearance (76). A significant decrease in the level of alkaline phosphatase (AP) activity was invariably observed, suggesting an overall reduction in osteoblast biosynthetic activity. Since serum AP is not solely derived from osteoblasts, decreased levels could also reflect reduced production from other tissue sources of this enzyme, e.g., liver and intestine, or, alternatively, a selectively accelerated clearance of this enzyme from the circulation (76a). However, the serum levels of osteocalcin, a protein made exclusively by osteoblasts and odontoblasts (76b), were also significantly reduced in lck-IL-4 mice compared to non-transgenic littermates. Together, these findings strongly suggested that decreased osteoblast activity had a significant role in the bone disorder of lck-IL-4 mice.

EXAMPLE 6

Expression of the lck-IL-4 transgene in lymphoid, bone marrow, and other tissues The generalized bone disease in lck-IL-4 mice might be due to a systemic or a local (bone microenvironment) effect mediated by expression of the transgene. Alternatively, the disease might reflect the disruption of an endogenous gene critical in bone remodeling as a result of transgene integration. To determine if there was detectable expression of the lck-IL-4 transgene in bone marrow cells, a finding which would make a local IL-4-mediated mechanism for osteoporosis plausible, these cells were assayed for spontaneous production of IL-4 using a sensitive bioassay [lower limit of detectability <10 pg/ml (35,77)]. Conditioned media from bone marrow cells (isolated by irrigation of humeri, femurs, and tibias) from lck-IL-4 or littermate control mice was prepared by incubating cells ($5\times10^6$/ml) in IL-4-free CT.4S medium (77) for 24 hr. Conditioned media from thymocytes, a cell type known to express high levels of the lck-IL-4 transgene (35), and from splenocytes, a cell type predicted to have low levels of transgene expression, were prepared in parallel. IL-4 activity was determined by the ability of conditioned media to support [$^3$H]thymidine incorporation by CT.4S cells as previously described (77). The concentration of IL-4 in samples was interpolated from a standard curve generated using recombinant murine IL-4. To confirm that [$^3$H]thymidine incorporation was IL-4 dependent, an aliquot of each sample was preincubated with saturating amounts of purified 11B11 [anti-murine IL-4 mAb (78)] for 45 min at 4° C. prior to the assay. Table 4 shows representative results from one of three experiments in which cells from 6-wk-old mice were analyzed. Spontaneous IL-4 production was detectable by transgenic thymocytes, but not by transgenic splenocyte or bone marrow cells. This result was not unexpected since the lck proximal promoter is mainly active in immature T-lineage cells. Neutralization of this thymocyte-derived activity by 11B11 mAb confirmed its identity as IL-4. As expected, none of the supernatants from these cell types in littermate controls had detectable activity.

Table 4. IL-4 secretion (pg/ml) by unstimulated cells from lck-IL-4 and littermate control mice.

| Cell Type | without 11B11 mAb | with 11B11 mAb |
|---|---|---|
| lck-IL-4 thymocytes | 29 | <10 |
| nontransgenic littermate thymocytes | <10 | ND |
| lck-IL-4 splenocytes | <10 | <10 |
| nontransgenic littermate splenocytes | <10 | ND |
| lck-IL-4 bone marrow | <10 | <10 |
| nontransgenic littermate bone marrow | <10 | ND |

Figure 5:
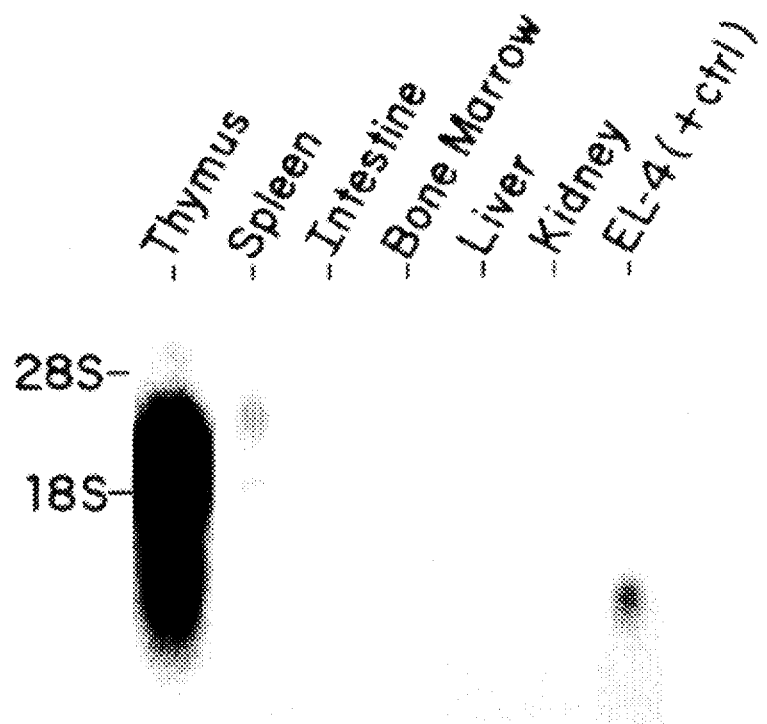
FIG. 5 (Prior Art) shows total RNA from tissues of lck-IL-4 mice hybridized with an IL-4 cDNA probe, as described in Example 6.

If bone-marrow derived IL-4 was responsible for the osteoporotic phenotype, the above negative results indicated that relatively low, nonpharmacologic levels of IL-4 were sufficient for this to occur. This is a reasonable possibility, given the potency of IL-4 in mediating many of its biologic activities (28,29) and the likelihood that any transgene expression in bone marrow would be constitutive. As an alternative to the IL-4 bioassay, we analyzed bone marrow from lck-IL-4 mice for IL-4 transcripts using RNA blotting. While transgene-derived transcripts were evident in thymus and spleen tissue, they were not detectable in bone marrow cells (FIG. 5). It should be noted that transgene-encoded IL-4 transcripts, which contain 3' hGH sequences (see FIG. 1), were significantly larger and readily distinguished from the endogenous 0.7-kb IL-4 transcripts found in EL-4 cells.

FIG. 5 (35) shows total RNA from tissues of lck-IL-4 mice hybridized with an IL-4 cDNA probe. All lanes were loaded with 10 μg. RNA from PMA-stimulated IL-4 cells, which express endogenous IL-4 gone transcripts, served as a positive control.

Given these negative results, we chose to determine the mount of IL-4 mRNA transcripts in bone marrow cells from lck-IL-4 mice using a highly-sensitive reverse transcriptase-polymerase chain reaction (RT-PCR) assay (79). Special precautions were taken to insure specificity and that the assay was at least semiquantitative. Two μg of total RNA from all samples were reverse-transcribed in parallel using a standard protocol (79). Various dilutions of the final RT reaction from each sample were amplified by PCR under identical conditions. To prevent amplification of any contaminating genomic DNA, murine IL-4 primers from the first and fourth exons, which are separated by more than 6 kb of genomic sequence, were used (80,81). PCR reaction products were electrophoresed and transferred to nylon filters by Southern blotting (71). The filters were hybridized with a murine IL-4 probe internal to both primers, to insure that detection of IL-4 sequences was specific. Scanning densitometry was used to quantitate the intensity of signals on autoradiographs of these filters. The portion of the curve for which RT concentration was linear with autoradiographic signal was then determined. In comparing autoradiographic signals from different samples, only an RT dilution which fell in this range of linear response was used. To control for possible differences between the efficiency of the reverse transcription reaction, the same RT dilution used to detect murine IL-4 mRNA was also used to amplify sequences for β-actin (82), an abundant housekeeping gene.

Figure 6A:
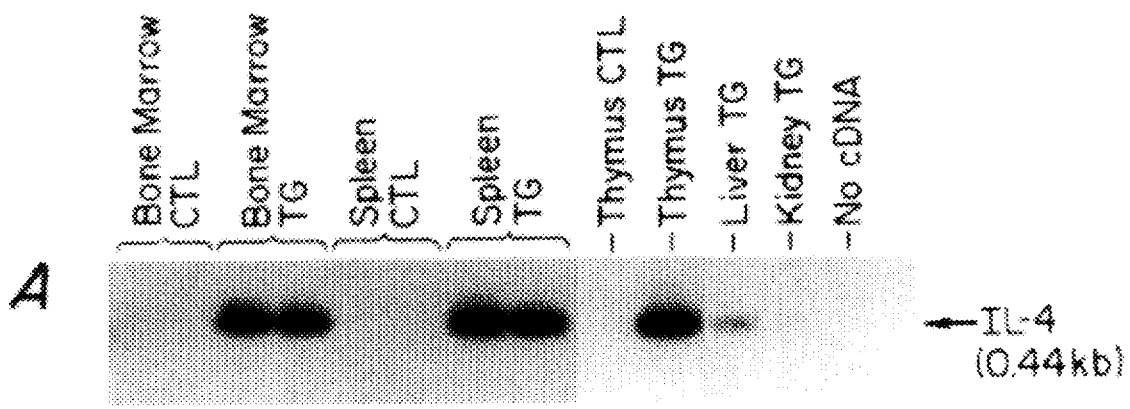
FIG. 6 shows levels of IL-4 mRNA transcripts in bone marrow and other tissues from lck-IL-4 mice, as described in Example 6.
Figure 6B:
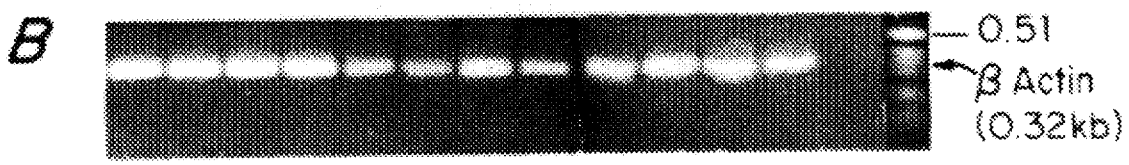

Using the RT-PCR assay described above, IL-4 mRNA was detectable in bone marrow and spleen cells, and thymocytes from lck-IL-4 mice, but was undetectable from these cells in nontransgenic littermates. FIG. 6 shows RNA levels in tissues from lck-IL-4 (TG) and nontransgenic littermates (CTL) assayed by RT-PCR. Spleen and bone marrow from two individual transgenic and control mice were assayed. FIG. 6A: PCR reaction products using first and fourth exon piers from the murine IL-4 gene, after Southern transfer and hybridization with an internal murine IL-4 cDNA probe. FIG. 6B: PCR reaction products using primers for β-actin after electrophoresis and ethidium bromide staining. All RT and PCR reactions shown were performed in parallel.

The low levels of IL-4 transcripts observed in transgenic kidney and liver tissue were presumably the result of blood contamination, since the endogenous proximal lck promoter segment is normally transcriptionally inactive in these tissues (39). The fact that the levels of IL-4 mRNA in bone marrow is markedly higher than kidney or liver argues against this merely representing blood contamination. The ready detection of IL-4 transcripts in spleen and thymic tissue from lck-IL-4 but not control mice was expected based on the results using RNA blotting (FIG. 5). The primer pair used to detect IL-4 in these assays does not distinguish between transgenic and endogenous IL-4 transcripts. However, the lack of detectable signals in any of the nontransgenic littermate samples indicated that virtually all IL-4 mRNA detected in transgenic samples was derived from the transgene. The similar amount of β-actin product in all samples suggested that the differences in IL-4 transcript levels were not attributable to differences in the overall efficiency of the reverse transcription reaction.

EXAMPLE 7

Determine whether the development of osteoporosis observed in lck-IL-4 mice depends on the production of IL-4 in vivo We hypothesize that this will require transgene expression, particularly within the bone microenvironment, and will not be due to the disruption by transgene integration of a genetic locus crucial for bone metabolism. We predict that: a) osteoporosis will occur reproducibly in independently generated lines of mice bearing the lck-IL-4 transgene, and that its severity will correlate with transgene expression by bone marrow cells; b) osteoporosis will depend on the presence of mature T cells, and will occur only after these cells appear in the periphery, including the bone marrow, during postnatal development; c) treatments which decrease transgene expression or neutralize secreted IL-4 will ameliorate osteoporosis; d) osteoporosis will be adoptively transferred to wild-type mice by bone marrow transplantation or by mature lck-IL-4 T cells; conversely, lck-IL-4 mice will be cured of osteoporosis by transplantation with wild-type bone marrow; and e) transgenic mice in which IL-4 production is targeted to osteoblasts using the osteocalcin promoter (ost-IL-4 mice) will also develop osteoporosis. If none of these predictions are correct, and the development of osteoporosis appears independent of the expression of IL-4 in vivo, one can, as an alternative approach, clone and characterize any endogenous genes which the lck-IL-4 transgene may have disrupted or altered by its integration in the initial line.

Additional lines of lck/IL-4 transgenic mice are generated and examined for evidence of osteoporosis or other bone disease using microradiography and histomorphometry after in vivo tetracycline labeling (see Materials and Methods below). If bone disease similar to that found in the #1315 line is observed in these additional lines, this implies that the construct per se, rather than a particular integration site, is responsible for this phenotype. Of interest on this point is the recent report by Tepper et al. (83) of mice with an IL-4 transgene under the control of the immunoglobulin heavy (μ H) chain enhancer. These mice displayed perturbed T-lineage cell development similar to that observed in lck-IL-4 mice, but it is not known if bone abnormalities were also present in these animals. Should μ H chain enhancer-IL-4 mice lack bone disease, this could reflect differences in the tissue pattern of transgene expression because of the promoter system used, and would not be informative as to whether insertional mutagenesis from transgene integration was likely to be the cause of osteoporosis in the #1315 lck-IL-4 line. For example, the lck promoter is active in NK cells (84), a cell type which does not normally express immunoglobulin genes. Hence, it is still important to generate additional lck-IL-4 mice for mechanistic studies.

The following studies are pursued for the #1315 line and any other lck-IL-4 lines manifesting bone disease:

1. Determine whether them is a positive correlation between the levels of transgene expression in the bone microenvironment and the severity of bone disease in lck-IL-4 transgenic mice. Transgene expression by bone marrow cells is compared to that by other tissues using RNase protection assays or reverse transcriptase-polymerase chain reaction (RT-PCR) (see above). Both assays are highly sensitive and do not require large amounts of total RNA to be performed. Although the RNase protection assay is more technically difficult to perform than RT-PCR, it is also a more quantitative assay, and is therefore the preferred approach.

2. To confirm that bone disease is dependent on IL-4 secretion, any lines manifesting bone disease are treated with anti-IL-4 monoclonal antibody (mAb) beginning at approximately two weeks of age (see section N, below, for details). This is a convenient age to begin treatment, since tailblots can be readily used to identify transgenic progeny. If we are unable to ameliorate or cure bone disease by anti-IL-4 treatment in the #1315 or other lines, one possibility would be that there is a critical developmental stage in bone, beyond which IL-4-induced abnormalities are irreversible. This would be more likely if there were evidence of bone disease in early ontogeny (see below). To address this possibility, we treat pregnant mice which have been mated with lck-IL-4 males with anti-IL-4 starting at day 10 of gestation. This precedes by several days the first detectable transcriptional activity of the endogenous proximal lck segment within the thymus and, presumably, the activity of the lck-IL-4 transgene as well. All progeny continue to be treated with anti-IL-4 for several weeks after birth. The anti-IL-4 antibody we use, 11B11 (78), has previously been shown to effectively cross the mouse placenta (Robert Tepper, personal communication). If treatment beginning in fetal life is still unsuccessful in partially or completely alleviating bone disease, this might reflect an inability to achieve high enough local concentrations of antibody at sites of IL-4 secretion. As an alternative approach, we use an anti-murine IL-4 receptor mAb (85) in place of, or in addition to, mAb 11B11. However, the absence of a blocking effect will still not exclude inadequate local concentrations of antibody. Therefore, regardless of the outcome of anti-IL-4 and/or anti-IL-4 receptor experiments, we proceed to determine the effect on bone disease of the transplantation of normal bone marrow as well as decreasing transgene expression by reducing or eliminating particular T-lineage or NK populations, as described below.

To determine if the osteoporosis of lck-IL-4 mice is mediated by hematopoietically derived cells, lck-IL-4 mice are irradiated and reconstituted with bone marrow from wild-type (nontransgenic) mice. Experiments in which normal mice are reconstituted with lck-IL-4 bone marrow are also performed to determine if this is sufficient to produce the osteoporotic phenotype. Since the #1315 line of lck-IL-4 mice has been backcrossed with homozygous C57BL/6 mice for more than 9 generations, it is essentially congenic on the C57BL/6 background, and should accept bone marrow from normal C57BL/6 donors. A failure to cure osteoporosis in lck-IL-4 mice by transplantation of normal bone marrow, or, conversely to adoptively transfer osteoporosis to wild-type mice by transplantation of lck-IL-4 marrow, could have several explanations. One would be that the osteoporotic phenotype is mediated by transgene-expressing cells which are not hematopoietically derived. This seems remote, given that the lck gene is not normally expressed by any nonhematopoietic cell type. A more likely explanation would be that the phenotype is due to transgene integration altering the function Of nonhematopoietic cells involved in bone remodeling. This possibility would be particularly likely if all of the predictions of the above study are incorrect. A final possibility is that osteoporosis is transgene-dependent, but is irreversible, or cannot be induced, after a critical development stage. This possibility cannot readily be addressed by transplanting bone marrow into mice younger than four to six weeks of age, since this results in an unacceptably high rate of mortality. However, other manipulations to reduce transgene expression in lck-IL-4 mice can be performed during the fetal or neonatal period of development to address this possibility. These are described below.

To test our hypothesis that the development of bone disease is mediated by mature peripheral T cells, we first determine when significant bone disease is first evident in post-natal development. Mature T cells do not begin to accumulate in significant numbers in the periphery until after birth (86) and do not reach peak adult levels until after 6–12 weeks of age. Therefore, if osteoporosis is dependent on the presence of mature peripheral T cells, it is unlikely that bone disease will occur before 2–3 weeks of age. We thymectomize neonatal lck-IL-4 and littermate controls to limit the accumulation of mature T cells and determine how this impacts on the development of osteoporosis. If thymectomy ameliorates or eliminates bone disease, we conclude that this phenotype is mediated by T-lineage cells which express the transgene. We then determine if elimination of mature T-lineage cells is sufficient to completely or partially prevent bone abnormalities. Lck-IL-4 mice are treated beginning in the neonatal period with monoclonal antibodies, such as anti-Qa-2 (86,87), which preferentially deplete mature peripheral T cells but leave the majority of thymocytes intact. If the elimination of peripheral T cells ameliorates or cures osteoporosis in lck-IL-4 mice, we perform adoptive transfer experiments to prove that T cells are sufficient to induce bone disease: Peripheral T cells are purified from the spleens and lymph nodes of lck-IL-4 mice, and injected intravenously into normal adult mice. If our ontogeny studies indicate that osteoporosis is evident relatively early in lck-IL-4 mice (i.e., before 2–3 weeks of age), T cells are injected intraperitoneally into normal neonatal mice. (The intravenous route is technically difficult until mice are about 2–3 weeks of age.) Recipient mice are analyzed at various times after injection for the development of osteoporosis, as described below. In the event that elimination of mature T cells does not ameliorate bone disease but thymectomy is effective, we conclude that it is likely that IL-4 is mediating its effect systemically on bone rather than by local secretion within the bone microenvironment.

If, contrary to our prediction, bone disease is evident in lck-IL-4 mice before two to three weeks of age, we still perform neonatal thymectomies to determine if disease is mediated by T-lineage cells. If thymectomy does not ameliorate bone disease, this suggests that transgene-mediated effects are likely to be due, at least in part, to expression by non-T lineage cells. NK cells and, to a much smaller extent, B cells are the only non-T lineage cell types which have been shown to express significant amounts of lck (37–39,84). Therefore, to determine if bone disease is mediated by NK cells, lck-IL-4 and control mice are treated with antibodies which effectively deplete NK cells in vivo, such as asialo-$GM_1$ antiserum (88) or mAb NK1.1 (89). Similar to the anti-IL-4 experiments described above, antibody treatments are initiated during pregnancy to attempt to deplete NK cells during fetal ontogeny. These NK cell depletion studies are also performed in the event that bone disease is not evident until after two weeks of age, but neither thymectomy nor the elimination of peripheral T cells effectively ameliorates bone disease.

3. If any of the above studies with lck/IL-4 mice indicate that osteoporosis is mediated by transgene expression, we proceed to generate new lines of mice with a transgenic construct in which the osteocalcin promoter is used to direct transcription of an IL-4 cDNA. Osteocalcin is produced exclusively by osteoblasts and odontoblasts (20,76), and the osteocalcin promoter has been characterized in some detail (90,91). Therefore, this promoter appears to be a reasonable choice by which to selectively increase IL-4 production within the bone microenvironment, and to determine whether this production is sufficient to cause severe osteoporosis. As an alternative approach, less well-characterized promoters from a number of other cloned bone matrix proteins (e.g., osteopontin) can be employed. If osteoporosis or other bone disease is observed in ost-IL-4 mice, we compare the mount of transgene expression in bone tissue by several independent lines generated with this construct, and determine if this positively correlates with the severity of disease. Analogous to the lck-IL-4 experiments outlined above, we also treat ost/IL-4 mice which manifest bone disease with anti-IL-4 and/or anti-IL-4 receptor mAbs to confirm that the disease is IL-4 dependent.

The fact that the osteoporotic phenotype of the #1315 line of lck-IL-4 mice has an autosomal dominant inheritance pattern suggests that disruption of an endogenous gene via transgene integration is probably not responsible for the bone disease. Most cases of insertional mutagenesis in transgenic mice have been expressed in an autosomal recessive pattern (92–97). However, if the osteoporosis is limited only to the #1315 line, and is not influenced by anti-IL-4 treatment, neonatal thymectomy, or apparently mediated by bone marrow-derived cells, we can critically examine the hypothesis that this phenotype is the result of transgene integration perturbing an endogenous genetic locus which is critical for normal bone remodeling. We prepare a genomic DNA library from the #1315 line and then clone and sequence the integration site and attempt to determine any gene product(s) which may have been perturbed. Although this approach has successfully been used by others to identify endogenous genes disrupted by transgene integration (92,98,99), there are a number of potential pitfalls to be considered. Transgene integration could perturb an endogenous genetic locus by a number of different mechanisms: The insertion of transgenic DNA within a genetic locus could prevent or reduce its expression, or alter the protein produced. This can occur as a result of either the deletion and/or rearrangement of flanking genomic DNA (92, 100, 101). Alternatively, the transgenic promoter could act to enhance expression of genes flanking the integration site; if the transgene acted as a locus activating region, such enhancement could potentially occur over more than 100 kb of genomic DNA (102). Regardless of the mechanism by which insertional mutagenesis might act to produce the phenotype, a major task would be to identify the affected gene products. This is not a trivial task since the size of mammalian genes varies from a few kilobases to more than 2 megabases. Although PCR-based techniques have recently been described which may identify functional exons within genomic DNA (103); see section O below), it remains to be shown that this procedure can reliably identify all such segments (103). Therefore, in the event of negative results with this technique, probes derived from nonrepetitive regions flanking the integration site, or from segments which have been deleted as a consequence of integration, are used to identify perturbed genes. The probes are used to screen for alterations in transcripts in bone marrow, osteoblasts, and other tissues from transgenic and normal animals. The chromosomal location of the transgene integration site is also determined and, if possible, more finely mapped by linkage analysis by crossing lck-IL-4 mice with appropriate mutant strains. This comprehensive approach offers the best chance for identifying a genetic locus which is critical in bone remodeling.

If an endogenous gene product which has been perturbed by transgene integration is identified, the scope of subsequent studies depends on whether this is a novel gene product. Assuming that it is previously undescribed, we determine which tissues express the gene's cognate mRNA. We particularly focus on characterizing mRNA expression by normal bone tissue cells, as well as relevant osteoblast and osteosarcoma cell lines. High priority is given to the generation of polyclonal and preferably monoclonal antibody reagents against the gene product, to determine protein expression by various tissues, particularly bone. These studies lay the groundwork for experiments to determine the normal function(s) of the cloned gene product.

EXAMPLE 8

Define alterations in osteoblast and/or osteoclasts which are responsible for osteoporosis in lck-IL-4 mice and, if applicable, ost-IL-4 mice We hypothesize that decreased osteoblast activity due to locally produced IL-4 will be a major mechanism for both types of transgenic mice, and predict that: a) osteoclast activity will be reduced, resulting in decreased bone remodeling; b) osteoblast activity will be depressed to a greater extent than osteoclast activity, accounting for progressive osteoporosis; c) osteoblast and osteoclast abnormalities will be ameliorated by manipulations which reduce transgene-mediated IL-4 production; and d) osteoporosis will not be associated with significant increases in mast cell abundance nor with major alterations in systemic hormones affecting bone metabolism.

These studies should substantially enhance our understanding of the pathogenesis of osteoporosis, and the role that IL-4 may play in this disease process. They may also point out potential pitfalls of systemic immunotherapy with cytokines such as IL-4.

The skeletal status of all lines of lck-IL-4 and ost/IL-4 mice are screened microradiographically and by routine histology. The remodeling dynamics of those with osteoporosis are examined histomorphometrically using double tetracycline labeling and nondecalcified histological sections. This approach enables one to qualitatively determine the effects of the transgene on the rates of bone formation (mineralization) and the numbers of osteoblasts and osteoclasts involved in the remodeling process. These examinations include stains to determine if the numbers of mast cells are increased in bone tissue from any of our transgenic lines. New lines are screened at 12 weeks of age. This should provide sufficient time for the expression of bone disease, based on our experience with the lck-IL-4 line, in which severe osteoporosis is readily apparent at 6 weeks of age. However, some mice are allowed to age for up to one year to insure that a late-appearing phenotype is not missed.

We specifically quantitate osteoblasts and osteoclasts in all lines which have evidence of bone disease using enzymo- and immuno-histochemical techniques. Osteoclasts are identified by staining bone in situ for tartrate-resistant acid phosphatase and osteoblasts by staining for alkaline phosphatase and osteocalcin using enzymatic and immunohistochemical techniques, respectively (104–107). To evaluate overall osteoblast activity, serum levels of osteocalcin and alkaline phosphatase are determined in affected mice and sex-matched littermate controls. Osteocalcin level is the preferred assay, because of its greater specificity for osteoblast activity than alkaline phosphatase level (20,76,108). Once these more detailed studies are completed, we then examine the effect of anti-IL-4 treatment and manipulations performed to reduce transgene expression (see above) on the severity of bone disease. For these experiments, microradiography, histomorphometry with tetracycline labeling, in situ assays of osteoblast and osteoclast function, and serum assays of osteoblast activity are employed.

Sera from lines which manifest bone disease are screened for endocrine and metabolic abnormalities, including total calcium, phosphorus, creatinine, total protein, PTH, corticosterone [the major circulating glucocorticoid in mice (109)] and osteocalcin concentrations as well as alkaline phosphatase activity. It is particularly important to exclude hyperglucocorticoidism since there are recent in vitro data that low concentrations of another T-cell derived cytokine, IL-2, can potentiate the release of anterior pituitary hormones, including ACTH (110). Further, our group has encountered patients with Cushings syndrome in whom osteoporosis has been the sole clinical manifestation.

MATERIALS AND METHODS

A. Transgene constructs. Purification of DNA plasmids, restriction endonuclease digestion, calf intestinal phosphatase-treatment of vectors, and ligation of DNA fragments use standard methods (71). Completed constructs are purified from vector sequences by restriction endonuclease digestion and electrophoresis onto DEAE-nitrocellulose paper (71), to result in DNA free of particulate matter which can interfere with microinjection. The sequences across ligation sites are verified by using standard dideoxynucleotide chain-termination sequencing methods (71).

For the generation of additional lines of lck-IL-4 mice, a candidate alteration from the construct used in the generation of the #1315 line is in the hGH segment. As discussed above, it is extremely unlikely that biologically significant amounts of hGH protein are produced by the lck-IL-4 transgene in vivo. However, this possibility can be completely excluded in all future transgene constructs by replacing the hGH segment with hGX, which carries a frameshift mutation in the hGH coding sequence (111). hGX protein has no significant biologically active in mice, even at high levels (111).

To make the ost-IL-4 transgene construct, the osteocalin promoter is subcloned immediately 5' to the hGX segment contained in the pBS/KS vector. The osteocalcin segment is either obtained from the laboratories in which it has been cloned and characterized (90,91), or is isolated by PCR amplification of murine genomic DNA. If PCR is used, primers include convenient internal restriction sites to facilitate subcloning. The murine IL-4 cDNA clone (69) is then inserted at a BamHI site in the 5' untranslated region of the first exon of hGX. The ost-IL-4 transgene construct is similar to the lck-IL-4 construct shown in FIG. 1, except that the osteocalcin promoter is substituted for the lck promoter segment 5', and the hGX segment is substituted for the hGH segment 3'. The human rather than murine osteocalcin promoter is used in this construct since it is readily available and has been well-characterized. The tissue-specificity of expression of transgenes driven by human promoters has matched that of homologous endogenous murine promoter in most instances. (data not shown). Our experience with the lck-IL-4 construct has been that its expression in vivo in mice is compatible with viability and fertility. However, other IL-4 transgenic mice generated by Tepper and colleagues (83), in which the transgene was transcriptionally driven by immunoglobulin heavy chain enhancer, uniformly died shortly after birth. This presumably was due to a toxic effect of IL-4. To attenuate expression of the transgene, these investigators inserted prokaryotic sequences between the promoter and IL-4 segments. For unknown reasons, prokaryotic sequences appear to generally inhibit transgene expression (112). Transgenic mice bearing these attenuated constructs were both viable and fertile. If expression of the ost-IL-4 occurs at high enough levels to interfere with either viability or fertility, constructs are redesigned to include attenuating prokaryotic sequences between the osteocalcin promoter and IL-4 cDNA. An alternative approach is to delete the hGX segment of the construct, replacing it with a polyadenylation signal segment; the lack of intronic sequences in this construct should also lead to lower levels of transgene expression.

B. Generation of transgenic mice and tailblots. Transgene construct DNA diluted in Tris-EDTA buffer is microinjected into the pronuclei of C57BL/6J X DBA/2J $F_2$ hybrid mouse zygotes. The injected embryos are transferred to the oviduct of female Swiss-Webster previously made pseudopregnant by mating with vasectomized SJL male mice. These pseudopregnant mice are anesthetized using an intraperitoneal injection of 0.4–0.5 ml of a solution of ketamine (6.5 mg/ml) and xylazine (0.4 mg/ml) in phosphate-buffered saline prior to the exteriorization of the oviduct. After embryos are transferred, the oviduct is returned to the pelvic cavity and the wound sutured closed.

Mice born to pseudopregnant mothers are screened at 2–3 weeks of age for integration of the transgene by the tailblot technique. To obtain tail tissue, mice are anesthetized using ether or a single 0.1 ml intraperitoneal injection of ketamine/xylazine solution described above. Approximately 1 cm of tail tissue is removed using a sharp scissors; after which the tail wound is electro-cauterized to stop bleeding. Mice are also ear-tagged at this point for identification purposes. Tail tissue is digested with proteinase K (250 µg/ml) in the presence of 1% SDS and Tris-EDTA buffer for 4 h at 37° C. Protein is precipitated by the addition of NaCl and KCl to final concentrations of 0.4M and 20 mM, respectively. The DNA contained in the supernatant is ethanol precipitated, dissolved in 0.1M NaOH/2M NaCl, boiled for three min., and dotted onto nitrocellulose filters. The filter is neutralized by moistening with 2× standard saline citrate [SSC (71)], baked at 80° C. for 1 h, and then hybridized with a 0.6-kb hGH probe (72) in Stark's buffer (113) at 42° C. for 12–24 h. Blots are then washed with 6× SSC, 0.1% SDS for 30 min, 0.1× SSC, 0.1% SDS for 30 min, and then autoradiographed.

Mice which are positive for transgenic constructs are backcrossed to C57BL/6 mice. Nontransgenic littermates are kept with transgenic littermates of the same sex to serve as wild-type controls for all experiments.

C. Cell isolation. Murine bone marrow cells are isolated by irrigation of femurs and humeri from euthanized mice with phosphate-buffered saline (PBS), pH 7.4. To isolate spleen or lymph node mononuclear cells, tissue is disrupted with a fine-mesh sieve, and the mononuclear fraction is purified by Ficoll-Hypague density gradient centrifugation (114). In cases of significant red blood cell contamination, brief hypotonic lysis with $NH_4Cl$ is performed (115). T lymphocytes are purified from splenic or lymph node mononuclear cells by passage over nylon wool (116) followed by treatment with mAb and complement to deplete B and monocyte-lineage cells as described (117). The purity of all final cell preparations are determined by immunofluorescent staining with appropriate mAbs analyzed by flow cytometry.

D. RNA isolation. Total cellular RNA is isolated from cells or tissue using the guanidinium isothiocyanate/CsCl method (118). The RNA pellet is dissolved in KNase-free water, ethanol precipitated in 0.3M Na acetate (pH 5.3), redissolved in RNase-free water, and quantitated by spectrophotometry. A small aliquot is also run on a Tris-borate agarose gel after brief heat denaturation in 50% formamide. Only those samples in which the 28S and 18S ribosomal RNA bands are intact are used for RNase protection or RT-PCR assays.

E. RNA blotting. Total RNA (5–20 µg/lane) is heat-denatured in 2.2M formaldehyde and 50% formamide and electrophoresed in 2.2M formaldehyde gels. The RNA is capillary transferred to nylon membranes using 20× SSC (pH 7.0). RNA is cross-linked to the membrane by brief exposure to short-wave UV light and then baked at 80° C. Filters are prehybridized with Stark's buffer (113) for 1–2 h at 42° C. and then hybridized with $^{32}P$-labeled DNA probes at $1–2\times10^6$ units/ml in Stark's buffer at 42° C. for 12–24 h. After hybridization, the blots are washed and autoradiographed as described above for tail blots.

F. RNase protection assays. Total RNA (0.1–2 µg) is denatured for 5–10 min at 85° C. in a mixture containing $1–2\times10^5$ cpm/tube of an antisense RNA probe, 80% formamide, 40 mM PIPES, 0.4M NACl, 1 mM EDTA. After overnight hybridization at 52°–53° C., the sample is incubated with RNase A (100 µg/ml) and RNase T1 (20 U/ml) for 30 min at room temperature, followed by digestion with proteinase K (500 µg/ml) for 30–45 min at 37° C. Both hybridization temperature and concentrations of RNase may be varied as needed depending on the particular probe. After phenol/chloroform extraction, the RNA remaining in the aqueous phase is ethanol precipitated in the presence of carrier tRNA, washed in 80% ethanol, desiccated, and redissolved in 80% formamide/TBE buffer. After heat-denaturation at 100° C. for 5 min, the samples are loaded onto a5% acrylamide, 8M urea sequencing gel, electrophoresed, and then autoradiographed at −80° C.

G. Reverse-transcriptase-polymerase chain reaction (RT-PCR) analysis. Total RNA (1–2 µg) is heat-denatured at 90° C. for 5 minutes, rapidly iced, and then allowed to anneal to random hexamers for 5 minutes at room temperature. Reverse-transcription using murine Moloney virus reverse transcriptase enzyme is performed at 42° C. for 1 hr as described (79). The reaction mixture is incubated at 95° C. for 5 minutes to denature the RT enzyme activity and is then stored at −80° C. until PCR is performed. For PCR, 1/1000th to 1/20th of the total RT reaction is amplified using 1 μM of specific 5' and 3' primers, 200 μM of all four dNTPs, and 40 U/ml of Taq polymerase in PCR buffer (Amersham Corp., Arlington Heights, Ill.). The reaction mixture is overlayered with mineral oil and then incubated in a thermal cycler. Standard reaction conditions are 30 cycles of denaturation at 95° C. for 1 min., annealing at 58° C. for 1 min., and extension at 72° C. for 2 min.

H. Southern transfer and hybridization. Aliquots of PCR reaction mixtures or restriction-endonuclease digested DNA are electrophoresed in Tris-borate agarose gels. The gel is sequentially soaked in 0.2N HCl for 10 min., 1.5M NaCl, 0.5N NaOH for 30 min, and 1M Tris-Cl (pH 7.4), 1.5M NaCl for 30 min. The DNA is then capillary transferred to nylon membrane (MSI, Lowell, Mass.) using 20× SSC (pH 7.0). The blot is UV shadowed while moist, baked at 80° C. for 1 hr, and then hybridized with $^{32}$P-labeled DNA probes ($1\times10^6$ cpm/ml) in Stark's buffer (113) for 6–18 hrs in a rotating oven at 42° C. In the analysis of PCR products, to prevent the detection of artifacts all probes should consist of sequences which are internal to the primers used for the PCR amplification. Blots are sequentially washed in 6× SSC, 0.1% SDS for 30 min. at 42° C., and 0.2× SSC, 0.1% SDS for 30 min. at 65° C. After washing, blots are autoradiographed at −80° C. in cassettes with intensifying screens. Scanning densitometry is used to quantitate the intensity of bands on autoradiographs.

I. Enzymo- and immunohistochemical analysis of bone tissue. Simultaneous determination of bone alkaline phosphatase and acid phosphatase activity in situ is performed using the protocol of Liu et al. (105). Tibiae and femora are fixed in 70% ethanol overnight and then embedded in glycolmethacrylate using an embedding kit (Polysciences) as described (105). Sections (5 μm) are cut with a sliding microtome, mounted, and air-dried. Sections are first stained for alkaline phosphatase activity by incubation with a mixture of naphthol ASTR phosphate and a coupling azo dye, Fast Blue BB, at pH 9.0 for 30 min at 37° C. After thorough rinsing with distilled water, the sections are stained for acid phosphatase activity by incubating with naphthol ASTR phosphate with hexazotized parasoaniline in the presence of tartrate (10 mM) at pH 5.0 at 37° C. for 1 hr. Using this procedure, alkaline phosphatase activity stains blue to purple while acid phosphatase activity stains red. This technique has been successfully used for murine, rat, as well as human bone tissue (105). Alternatively, separate staining procedures can be performed for acid phosphatase and alkaline phosphatase activity as previously described (104, 106).

Osteocalcin is detected immunohistochemically using a modification of the method of Ohta et al. (107). Bone tissue is rapidly fixed in periodate-lysine-paraformaldehyde solution at 4° C. for 6 hr. The tissue is rinsed in 20% polyethylene glycol (MW 20,000±5,000) in PBS (pH 7.4) and frozen in liquid nitrogen. Sections (5 μm) are cut on a cryostat and mounted on albumin-coated slides. Slides are incubated with 0.6% hydrogen peroxide in methanol for 30 min at room temperature to block endogenous peroxidase activity. Sections are then sequentially incubated in 5% skim milk, goat anti-mouse osteocalcin antibody (Biomedical Technologies, Stoughton, Mass.), peroxidase-conjugated F(ab')$_2$ fragments of donkey anti-goat IgG (Pel-Freez, Rogers, Ark.), followed by rinsing in complete Graham-Karnovsky medium (0.03% 3,3'-diaminobenzidine, 0.01% H$_2$O$_2$ in 0.05 Tris-HCl, pH 7.6). Sections are mounted on glycerin-agar.

J. Serum endocrine and metabolic studies. Serum osteocalcin and corticosterone are determined using commercially available RIA kits [osteocalcin: Biomedical Technologies, Stoughton, Mass.; corticosterone: Analytics, Gaithersburg, Md.). The osteocalcin assay only requires 10 μl of serum to be performed. The remaining hormone assays require 50 μl of serum per test. Serum calcium, phosphorus, creatinine, total protein concentrations, and alkaline phosphatase enzyme activity are measured using a Kodak EktaChem 700XR Analyzer. The analyzer requires 10 μl of serum or plasma per test. Blood (0.20 ml) can be drawn from the retro-orbital plexus of transgenic and littermate control mice every two weeks until sufficient serum is available for these studies. Serum is isolated from blood using Microtainer serum separators (Beeton Dickinson), a system which maximizes serum recovery from small blood volumes. Blood draws of this amount and frequency are well-tolerated and do not result in anemia. Serum for PTH assays is obtained from animals which are to be sacrificed for histomorphometric studies. Approximately 400–500 μl of serum can be obtained from a single adult mouse by cardiac puncture immediately after euthanasia. Biologically active murine PTH is measured using an RIA developed for the rat which crossreacts with murine PTH. This assay requires 200 μl of serum per test.

K. Bone histomorphometric analysis. Mice receive intraperitoneal injection of 30 mg/kg of tetracycline hydrochloride in sterile normal saline days 5 and 2 before sacrifice. All mice are injected at approximately 10 AM to avoid possible interference with skeletal circadian rhythmicity (115). Mice are euthanized and fixed in cold neutral formalin. The third caudal vertebrae is taken, and nondecalcified sections histomorphometrically quantitated according to the method of Marie et al. (119).

L. Microradiography. Formalin-fixed mice or disarticulated mouse skeletal tissues are washed, patted dry, and placed on a thin sheet of polyethylene film that is in contact with either Kodak high-resolution film or type 1-A glass plates. Radiographs are exposed in a Hewlett-Packard Faxatron 805 unit at 90 kV for 90 min at a focal film distance of 60 cm (120,121). Microradiographs are photographed with a Wild-Heebruge M-400 Photomakroskop camera system using Tech-Pan film. The film is developed in HC-110 developer, solution B for 5 min at 68° F.

M. Bone marrow chimeras and adoptive transfer. Mice are irradiated with 1000 Rads from a cesium source and on the same day are injected intravenously with $1\times10^7$ bone marrow cells. Chimeras are analyzed 6–12 weeks later for reconstitution by immunofluorescent staining of peripheral blood cells for T and B lymphocyte markers. These studies are performed using transgenic (lck-IL-4) donors and wild-type recipients congenic for the C57BL/6 background. If disease is transferred by bone marrow transplantation, some wild type recipients are thymectomized prior to transplantation to determine if the osteoporotic phenotype requires the presence of donor-derived T-lineage cells. In addition, unirradiated wild-type mice are injected with $5\times10^6$ purified peripheral T cells from lck-IL-4 mice, to determine if this is sufficient to cause osteoporosis. The converse experiment; transplantation of normal (C57BL/6) bone marrow into lck-IL-4 mice; is also performed, to determine if this procedure cures them of the osteoporotic phenotype.

N. In vivo antibody treatments. Mice are given weekly 10 mg injections of purified monoclonal antibodies (mAbs against IL-4, IL-4 receptor, NK1.1, or Qa-2) or asialo-GM$_1$ antisera (78,85,87–89). The asialo-GM$_1$ antisera is available from commercial sources (Wake Chemicals, Richmond, Va.). For mice younger than three weeks of age the intraperitoneal route is used. For mice older than three weeks of age, the intravenous route is used, since this is technically feasible and insures that systemic levels of antibody are achieved. Most of the perturbations of thymic development in lck-IL-4 mice are reversed by four weekly injections of anti-IL-4 mAb given either IV or IP (35).

O. Cloning and characterization of the transgenic integration site. In the event that the osteoporotic phenotype of the #1315 line of lck-IL-4 mice is unique to this line, and does not appear to be IL-4-mediated, the transgenic integration site in these animals is cloned. A genomic library for the #1315 line is prepared by standard methods: High-molecular weight genomic DNA is isolated from splenocytes by digestion in proteinase K (100 µg/ml) in digestion buffer (122) for 12–18 hr at 50° C. The digest is sequentially extracted with phenol, phenol-chloroform, and chloroform. The aqueous phase is dialyzed against 100 volumes and two changes of TE buffer for 24 hrs at 4° C. Restriction digestion of the DNA is necessary for it to be ligated into phage vectors. To determine the most appropriate restriction enzyme for this purpose, Southern blots, in which the genomic DNA has been digested with various enzymes which cut the lck-IL-4 transgenic construct internally, are hybridized with an hGH segment probe. Genomic DNA is digested with a restriction enzyme which yields hGH-genome fragments between 10–20 kb in size and for which there is a site in a λ cloning vector. Ideally, the enzyme yields fragments in this size range for both sides of the integration site. A variety of λ vectors with various cloning sites are commercially available for this purpose (e.g., Stratagene). The restricted DNA is size-fractionated on sucrose gradients to enrich for the desired fragment (123). This size-fractionated DNA is ligated to a compatibly-digested λ vector to produce a subgenomic DNA library. Small-scale test ligations are initially performed using a set amount of vector and varying amounts of insert. The conditions which result in the greatest number of phage clones when packaged and plated on host bacteria are then used in a large scale reaction. A library of about 500,000 clones should be more than sufficient to include the integration site. Phage plaques bound to nitrocellulose filters are denatured in 0.2M NaOH/1.5M NaCl, neutralized with 0.4M Tris-Cl/2× SSC (pH 7.6) and then 2× SSC. The filters will be baked for 90 min in vacuo at 80° C., and then hybridized with an hGH segment probe. Hybridization conditions are as described above for tailblots. Positive plaques are confirmed and purified by repetitive screening.

DNA inserts in positive plaques are subcloned into plasmids or, if applicable, directly excised as phagemids by co-infection with helper phage, e.g., in λ Zap vectors (Stratagene). Subcloned inserts are characterized by restriction mapping and by dideoxynucleotide chain termination sequencing. Genomic fragment segments in these inserts are used to probe Southern blots of genomic DNA from transgenic and nontransgenic #1315 littermates to determine if genomic DNA flanking the integration site has been deleted and/or rearranged. The isolation of these deleted sequences requires additional screening of genomic libraries from normal mice using genomic DNA probes contiguous to the transgene integration site. Normal murine genomic phage libraries suitable for this purpose are available from commercial sources. Once sequences which are contiguous to the transgene or have been deleted by its integration are isolated in phage clones, they are analyzed for the presence of coding sequences using the exon amplification strategy of Buckler et al. (103). This is a PCR-based procedure which identifies exon sequences within genomic DNA which have functional 5' and 3' splice acceptor sites. Genomic DNA sequences to be analyzed are subcloned into the cloning site of the pSPL1 vector (103). The vector is electroporated into COS-7 cells. Cytoplasmic RNA is isolated from the cells 48–72 hrs later. The RT procedure is performed as described above in section F, except that a 3' primer contained in the vector is substituted for random hexamers. The RT reaction is subjected to PCR amplification using appropriate 5' and 3' vector exon primers as described (103). PCR products are analyzed by agarose gel electrophoresis and ethidium bromide staining. Products which contain potential exon inserts are cloned and sequenced. If the obtained sequences are novel or incompletely characterized for their expression in bone tissue, they are $^{32}$P-labeled by the random primer method and used to probe RNA blots containing samples from various tissues, including bone marrow and whole bone tissue, as well as osteoblast and osteosarcoma cell lines. In the event that this PCR procedure does not identify functional genes in flanking DNA, an alternative approach is to screen for transcripts using probes derived from nonrepetitive regions of genomic DNA which flank or are deleted at the integration site. These probes are also used to test for the presence of homologous sequences in human genomic DNA using the Southern Blot technique. This approach contributed importantly to the successful cloning of the cystic fibrosis gene by positional methods (124). The integration site is also mapped using in situ chromosomal analysis (see below); (125). Once the chromosomal region of transgene integration is determined, linkage analysis is performed by crossing lck-IL-4 mice with available informative strains of mice whose mutations map to this region, to permit more detailed mapping of the integration site.

Those probes which detect novel RNA transcripts are then used to screen appropriate cDNA libraries to obtain the complete cDNA coding sequence. If novel cDNAs are found which have been disrupted or deleted by transgene integration, polyclonal antiserum against these gene products is generated to help further characterize their expression in tissues. The amino acid sequence of the gene product is deduced from the cDNA sequence. Peptides of the predicted protein which are hydrophilic and 10–15 residues in length are made using an automated solid-phase peptide synthesizer. The peptides are conjugated with and used to immunize rabbits as previously described (126). Subsequent experiments to determine the role of these gene products in bone remodeling depend, in large part, on clues to their function provided by previously cloned homologous gene products.

P. Chromosomal in situ hybridization. Metaphase chromosome spreads are prepared from PHA-stimulated C57BL/6 murine lymph node cells using standard cytogenetic methods (127). Chromosomal in situ hybridization is performed according to the method of Morton et al. (128) using high-specific activity tritiated DNA probes. After washing, slides are stained with 0.005% quinacrine mustard dihydrochloride. Metaphases are evaluated for hybridization by microscopy using a combination of incident ultraviolet and transmitted visible light (128).

Q. Vertebrate animals.
(1) Mice may be used exclusively in these experiments. The following is a listing of the strains, ages, sex, and numbers of animals which can be used for the described work:
   a) C57BL/6 mice bearing the lck-IL-4 and, potentially, the ost-IL-4 transgene, are bred.
   b) C57BL/6×DBA/2 $F_1$; both sexes; 5–20 weeks old. These mice are bred together. $F_2$ mouse zygotes obtained from these mice are microinjected with transgene constructs and then transferred to the oviducts of pseudopregnant female Swiss-Webster mice.

c) Swiss-Webster; females; 5–20 weeks old. These mice are used as surrogate mothers for embryos after their microinjection. They are induced into a pseudopregnant state by mating with vasectomized SJL male mice.

d) SJL; male; 5–20 weeks old. These mice are vasectomized and then mated with Swiss-Webster mice to induce a pseudopregnant state suitable for embryo transfer.

e) C57BL/6; both sexes; 5–20 weeks old. These mice are bred with transgenic founders and progeny to maintain transgenic lines.

f) BALB/c nude (nu/nu); females; 5–20 weeks of age. These mice are used to produce ascites containing high titers of anti-IL-4, anti-IL-4 receptor, anti-Qa-2, anti-NK1.1 monoclonal antibodies. These antibodies are then purified from ascites and used for in vivo treatments as discussed above.

(2) The lck-IL-4 murine model of osteoporosis is unique, since to our knowledge, no other animals develop severe generalized osteoporosis on a genetic basis. Mice are also ideal animals for performing studies in which various components of the immune system, e.g., T-lineage cells and/or NK cells, are depleted. The monoclonal antibody reagents and procedures necessary for these in vivo experiments have been extensively developed for use in rodents.

Citations

1. Whyte MP, et al. Amer J Med 72:193–202, 1982.
2. Culliton BJ. Science 235:833–834, 1987.
3. Stevenson JC. Obstet & Gynecol 75(S):36S–41S, 1990.
4. Schot LPC, et al. J Steroid Biochem Molec Biol 37:167–182, 1990.
5. Consensus Development Conference. Amer J Med 90:107–110, 1991.
6. Jackson JA, et al. Medicine 69:137–152, 1990.
7. Parfitt AM. Calcif Tissue Int 36:S37–S45, 1984.
8. Mundy GM. Recent Prog Hormone Res 45:507–531, 1989.
9. Parfitt AM, et al. In Osteoporosis, C. Christiansen et al. (eds). Proceedings from the Copenhagen Intl Symp on Osteoporosis, Jun. 3–8, 1984, Aalborg Stiftsbogtrykkeri, pp. 111–120.
10. Mundy GR. Bone 8(Suppl 1):S9–S16, 1987.
11. Yoshida H, et al. Nature 345:442–443, 1990.
12. Soriano P, et al. Cell 64:693–702, 1991.
13. Nowak R. J NIH Res 3:54–58, 1991.
14. Thomson BM, et al. J Exp Med 164:104–112, 1986.
15. Thomson BM, et al. J Immunol 138:775–779, 1987.
16. McSheehy PMJ, et al. J Clin Invest 80:425–429, 1987.
17. Mundy GR, et al. Ann NY Acad Sci 593:91–97, 1990.
18. Canalis E, et al. Annu Rev Med 42:17–24, 1991.
19. Stein GS, et al. FASEB J 4:3111–3123, 1990.
20. Robey PG. Endocrinol Metabol Clin N Amer 18:859–902, 1989.
21. Van PT, et al. Cell Tissue Res 225:283–292, 1982.
22. Malone JD, et al. J Cell Biol 92:227–230, 1982.
23. Saffar JL, et al. Bone 11:369–372, 1990.
24. Fallon MD, et al. Calcif Tissue Int 35:29–31, 1983.
25. Silberstein R, et al. Bone 12:227–236, 1991.
26. Galli SJ. Lab Invest 62:5–33, 1990.
27. Witte ON. Cell 63:5–6, 1990.
28. Paul WE, et al. Ann Rev Immunol 5:429–459, 1987.
29. Jansen JH, et al. Blut 60:269–274, 1990.
30. Postlethwaite AE, et al. J Clin Invest 87:2147–2152, 1991.
31. Howells G, et al. Eur J Immunol 21:97–101, 1991.
32. Satoh T, et al. Proc Natl Acad Sci USA 88:3314–3318, 1991.
33. Finkelman FD, et al. Proc Natl Acad Sci USA 83:9675, 1986.
34. Finkelman FD, et al. J Immunol 141:2335, 1988.
35. Lewis DB, et al. J Exp Med 173:89–100, 1991.
36. Garvin AM, et al. Mol Cell Biol 8:3058–3064, 1988.
37. Perlmutter RM, et al. Biochem Biophys Acta 948:245–262, 1988.
38. Perlmutter RM, et al. J Cell Biochem 38:117–126, 1988.
39. Marth JD, et al. Cell 43:393–404, 1985.
40. Carding SR, et al. Proc Natl Acad Sci USA 86:3342, 1989.
41. Palacios R, et al. EMBO J 16:91, 1987.
42. Barcena A, et al. J Exp Med 172:439, 1990.
43. Garvin AM, et al. Internatl Immunol 2:173, 1990.
44. Watanabe K, et al. Biochem Biophys Res Commun 172:1035–1041, 1990.
45. Shioi A, et al. J Cell Biochem, in press, 1991.
46. Hart PH, et al. Proc Natl Acad Sci USA 86:3803–3807, 1989.
47. Standiford TJ, et al. J Immunol 145:1435–1439, 1990.
48. Lehn M, et al. J Immunol 143:3020–3024, 1989.
49. Standiford TJ, et al. Biochem Biophys Res Commun 171:531–536, 1990.
50. Rennick D, et al. Proc Natl Acad Sci USA 84:6889–6893, 1987.
51. Lacey DL, et al. J Bone Mineral Res 6(supplement 1):S255, 1991.
52. Imai Y, et al. J Bone Mineral Res 5:393–399, 1990.
53. Rosen CJ, et al. J Bone Mineral Res 5:851–855, 1990.
54. Ernst DN, et al. J Immunol 145:1295–1302, 1990.
55. Lewis DB, et al. Proc Natl Acad Sci USA 85:9743–9747, 1988.
56. Lewis DB, et al. J Clin Invest 87: 194–202, 1991.
57. Pacifici R, et al. Proc Natl Acad Sci USA 84:4616–4620, 1987.
58. Killar LM, et al. Eur J Immunol 19:2205–2210, 1989.
59. Brown MA, et al. Cell 50:809–818, 1987.
60. Fallon MD, et al. Human Pathol 12:813–820, 1981.
61. Harvey JA, et al. Bone 10:237–241, 1989.
62. Leung DY, et al. Hematol/Oncol Clin N Amer 2:81–100, 1988.
63. Vercelli D, et al. J Clin Invest 85:1666–1671, 1990.
64. Kalu DN, et al. Endocrinology 124:7–16, 1989.
65. Matzsch T, et al. Thrombosis and Haemostasis 56:293–294, 1986.
66. Glajchen N, et al. Calcif Tissue Int 43:277–280, 1988.
67. Tsuboyama T, et al. Bone 10:269–277, 1989.
68. Bancherau J, et al. Bull Cancer (Paris) 78:299, 1991.
68a. Lian J, et al. Proc Natl Acad Sci USA 86:1143, 1989.
69. Noma Y, et al. Nature (Lond.) 319:640, 1986.
70. Chaffin KE, et al. EMBO J 9:3821–3829, 1990.
71. Maniatis T, et al. Cold Spring Harbor Laboratory Press, Cold Spring Harbor, N.Y., 1982.
72. Seeburg PH. DNA (NY) 1:239, 1982.
73. Brinster RL, et al. Proc Natl Acad Sci USA 85:836–840, 1988.
74. Brinster RL, et al. Proc Natl Acad Sci USA 82:4438, 1985.
74a. Garn SM, et al. Radiology 100:509, 1971.
74b. Riggs BL, et al. New Eng. J. Med. 314:1676, 1986.

75. Teitelbaum SL. Human Pathol 15:306–323, 1984.
75a. Marie P J, et al. Metabol. 34:777, 1985.
76. Spiegel AM. J. Bone Miner. *Res.* 6:515, 1991.
76a. Moss DW. Clin. Biochem. 20:225, 1987.
76b. Robey PG. Endocrin. Metabol. Clin. N. Amer. 18:859, 1989; Price PA, et al. J. Clin. Invest. 66:878, 1980.
77. Hu-Li J, et al. J Immunol 142:800, 1989.
78. Ohara J, et al. Nature (Lond) 315:333, 1985.
79. Kawasaki ES. IN PCR Protocols: A Guide to Methods and Applications. Academic Press, 1990, pp. 21–27.
80. Mohler KM, et al. J Immunol 145:1734–1739, 1990.
81. Otsuka T, et al. Nucleic Acids Res 15:333–344, 1987.
82. Brenner CA, et al. BioTechniques 7:1096–1103, 1989.
83. Tepper RI, et al. Cell 62:457–467, 1990.
83a. Burstein HJ, et al. J Immunol 147:2950–2956, 1991.
83b. Müller, et al. Eur J Immunol 21:921–925, 1991.
84. Biondi A, et al. Eur J Immunol 21:843–846, 1991.
85. Beckmann MP, et al. J Immunol 144:4212–4217, 1990.
86. Fowlkes BJ, et al. Adv Immunol 44:207–262, 1989.
87. Sharabi Y, et al. J Exp Med 171:211–219, 1990.
88. Gately MK, et al. J Immunol 141:189–200, 1988.
89. Koo GC, et al. Hybridoma 3:301, 1984.
90. Kerner SA, et al. Proc Natl Acad Sci USA 86:4455, 1989.
91. Schule R, et al. Cell 61:497–504, 1990.
92. Woychik RP, et al. Nature 318:36, 1985.
93. Ratty AK, et al. Molecular Brain Res 8:355–358, 1990.
94. Bier DR, et al. Genomics 4:498–504, 1989.
95. Xiang X, et al. Science 247:967–969, 1991.
96. McNeish JD, et al. Science 241:837–839, 1988.
97. Covarrubias L, et al. Mol Cell Biol 7:2243–2247, 1987.
98. Woychik RP, et al. Nature 346:850, 1990.
99. Maas RL, et al. Nature 346:853, 1990.
100. Bishop JO, et al. Mol Biol Med 6:283–298, 1989.
101. Covarrubias L, et al. Proc Natl Acad Sci USA 83:6020–6024, 1986.
102. Forrester WC, et al. Genes Develop 4:1637–1649, 1990.
103. Buckler AJ, et al. Proc Natl Acad Sci USA 88:4005–4009, 1991.
104. Fallen D, et al. Calcif Tissue Int 33:281–282, 1981.
105. Liu C, et al. Histochem 86:559–565, 1987.
106. Chappard D, et al. Basic Appl Histochem 27:75–85, 1983.
107. Ohta T, et al. Virchows Arch A Pathol Anat 415:459–466, 1989.
108. Lian JB, et al. J Clin Orthop Rel Res 226:267–291, 1988.
109. Depaolo LV, et al. In The Clinical Chemistry of Laboratory Animals, WF Loeb et al. (eds), Pergamon Press, p 279–308, 1989.
110. Karanth S, et al. Proc Natl Acad Sci 88:2961–2965, 1991.
111. Idzerda RL, et al. Molec Cell Biol 9:5154–5162, 1989.
112. Palmiter RD, et al. Annu Rev Genetics 20:61, 1986.
113. Cosman D, et al. Nature (Lond) 312:768–771, 1984.
114. Boyum A. Tissue Antigens 4:269, 1974.
115. Mishell BB, et al. Selected Methods in Cellular Immunology, WH Freeman and Co Pub, NY, 1980, pp. 3–27.
116. Julius MH, et al. Eur J Immunol 3:645–649, 1973.
117. Hathcock K. In Current Protocols in Immunology, J Coligan, et al. (eds), J Wiley & Sons, 1991, p. 3.3.1.
118. Glisin V, et al. Biochemistry 13:2633, 1974.
119. Marie PJ, et al. Metabolism 34:777–783, 1985.
120. Effman EL. In Models and Techniques in Medical Imaging Research, E Milne et al. (eds), Praeger, 1983, p. 164–181.
121. Effman EL. Invest Radiol 17:529–538, 1982.
122. Strauss WM. In Current Protocols in Molecular Biology, FM Ausubel et al. (eds), J Wiley & Sons, 1991, p 2.2.1.
123. Weis JH, et al. Ibid, p 5.3.1.
124. Rommens JM, et al. Science 245:1059–1065, 1989.
125. Marth JD, et al. Proc Natl Acad Sci 83:7400–7404, 1986.
126. Marth JD, et al. EMBO J 6:2727–2734, 1987.
127. Moorhead, et al. Exp Cell Res 20:613–616, 1960.
128. Morton CC, et al. Am J Hum Genet 36:576–585, 1984.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of increasing osteoblast activity in a mammalian host that exhibits decreased bone formation and increased IL-4 production as compared with a normal mammalian host of the same species, comprising the step of administering an IL-4 antagonist to the mammalian host, said antagonist specifically blocking the normal IL-4/IL-4 receptor interaction, in an amount effective to increase the serum level of osteocalcin in the mammalian host, wherein the antagonist comprises an IL-4 specific antibody, an IL-4 receptor specific antibody, an IL-4 receptor polypeptide or fragment thereof, or a soluble IL-4 receptor.

* * * * *

UNITED STATES PATENT AND TRADEMARK OFFICE
CERTIFICATE OF CORRECTION

PATENT NO. : 5,714,146
DATED : February 3, 1998
INVENTOR(S) : D.B. Lewis et al.

It is certified that error appears in the above-identified patent and that said Letters Patent is hereby corrected as shown below:

| COLUMN | LINE | |
|---|---|---|
| [56] Pg. 1, col. 1 | Refs. Cited (U.S. Pats, Item 2) | "Abraams" should read --Abrams-- |
| [56] Pg. 1, col. 1 | Refs. Cited (Foreign Pats.) | please insert --WO89/06975-- |
| [56] Pg. 1, col. 2 | Refs. Cited (Other Pubs., Item 10) | "idiopathis" should read --idiopathic-- |
| [56] Pg. 1, col. 2 | Refs. Cited (Other Pubs., Item 13) | "S45,1984" should read --S45. 1984-- |
| [56] Pg. 2, col. 1 | Refs. Cited (Other Pubs., Item 18) | "I.A." should read --K.A.-- |
| [56] Pg. 2, col. 1 | Refs. Cited (U.S. Pats, Item 20) | "oncogens" should read --oncogenes-- |

UNITED STATES PATENT AND TRADEMARK OFFICE
CERTIFICATE OF CORRECTION

PATENT NO. : 5,714,146
DATED : February 3, 1998
INVENTOR(S) : D.B. Lewis et al.

Page 2 of 6

It is certified that error appears in the above-identified patent and that said Letters Patent is hereby corrected as shown below:

| COLUMN | LINE | |
|---|---|---|
| [56] Pg. 2, col. 1 | Refs. Cited (U.S. Pats, Item 22) | "rearrange" should read --rearranged-- |
| [56] Pg. 2, col. 1 | Refs. Cited (U.S. Pats, Item 25) | "1439.1990" should read --1439, 1990-- |
| [56] Pg. 2, col. 1 | Refs. Cited (U.S. Pats, Item 27) | after "R.S. Geha" please insert --.-- |
| [56] Pg. 2, col. 1 | Refs. Cited (U.S. Pats, Item 27) | "Hypr-IgE" should read --Hyper-IgE-- |
| [56] Pg. 2, col. 1 | Refs. Cited (U.S. Pats, Item 28) | "Hollis,The Aged" should read --Hollis. The aged-- |
| [56] Pg. 2, col. 1 | Refs. Cited (U.S. Pats, Item 29) | "Osergaard" should read --Ostergaard-- |

UNITED STATES PATENT AND TRADEMARK OFFICE
CERTIFICATE OF CORRECTION

PATENT NO. : 5,714,146
DATED : February 3, 1998
INVENTOR(S) : D.B. Lewis et al.

It is certified that error appears in the above-identified patent and that said Letters Patent is hereby corrected as shown below:

| COLUMN | LINE | |
|---|---|---|
| [56] Pg. 2, col. 1 | Refs. Cited (U.S. Pats, Item 30) | "int he" should read --in the-- |
| [56] Pg. 2, col. 2 | Refs. Cited (U.S. Pats, Item 37) | "Abbs" should read --Abbas-- |
| [56] Pg. 2, col. 2 | Refs. Cited (U.S. Pats, Item 38) | "hyperexperssion" should read --hyperexpression-- |
| [56] Pg. 2, col. 2 | Refs. Cited (U.S. Pats, Item 40) | "Deried" should read --Derived-- |
| [56] Pg. 2, col. 2 | Refs. Cited (U.S. Pats, Item 42) | after "J.S." insert --Abrams, B. Boyce, H. Broxmeyer, and S.C. Manolagas. Increased-- |
| [56] Pg. 2, col. 2 | Refs. Cited (U.S. Pats, Item 42) | "deelopment" should read --development-- |

UNITED STATES PATENT AND TRADEMARK OFFICE
CERTIFICATE OF CORRECTION

PATENT NO.   : 5,714,146
DATED        : February 3, 1998
INVENTOR(S)  : D.B. Lewis et al.

It is certified that error appears in the above-identified patent and that said Letters Patent is hereby corrected as shown below:

| COLUMN | LINE | |
|---|---|---|
| 1 | 53 | "mount" should read --amount-- |
| 2 | 51 | "abrablasts" should read --fibroblasts-- |
| 2 | 57 | "in viva" should read --in vivo-- |
| 4 | 63 | "gone" should read --gene-- |
| 4 | 65 | "gone" should read --gene-- |
| 10 | 62 | "#1453" should read --#4453-- |
| 11 | 65 | "values±standard" should read --values ± standard-- |
| 13 | 8 | "mice. Although" should read --mice.  Although-- |
| 13 | 31 | "gone as a remit" should read --gene as a result-- |
| 13 | 42 | "values±the" should read --values ± the-- |
| 14 | 51 | "EktaChem700XR" should read --EktaChem 700XR-- |
| 14 | 54 | "Sloughton" should read --Stoughton-- |
| 14 | 55 | "values±the" should read --values ± the-- |

UNITED STATES PATENT AND TRADEMARK OFFICE
CERTIFICATE OF CORRECTION

PATENT NO. : 5,714,146
DATED : February 3, 1998
INVENTOR(S) : D.B. Lewis et al.

It is certified that error appears in the above-identified patent and that said Letters Patent is hereby corrected as shown below:

| COLUMN | LINE | |
|---|---|---|
| 16 | 34 | "gone" should read --gene-- |
| 16 | 37 | "mount" should read --amount-- |
| 17 | 4 | "piers" should read --primers-- |
| 18 | 18 | "them" should read --there-- |
| 19 | 17 | "Of" should read --of-- |
| 20 | 34 | "mount" should read --amount-- |
| 20 | 65 | "92, 100," should read --92,100,-- |
| 24 | 24 | "KNase" should read --RNase-- |
| 24 | 46 | "NACl" should read --NaCl-- |
| 24 | 58 | "a5%" should read --a 5%-- |
| 25 | 13 | "NACl" should read --NaCl-- |
| 25 | 24 | "at42°" should read --at 42°-- |
| 26 | 15 | "Beeton" should read --Becton-- |

UNITED STATES PATENT AND TRADEMARK OFFICE
CERTIFICATE OF CORRECTION

PATENT NO. : 5,714,146
DATED : February 3, 1998
INVENTOR(S) : D.B. Lewis et al.

It is certified that error appears in the above-identified patent and that said Letters Patent is hereby corrected as shown below:

| COLUMN | LINE | |
|---|---|---|
| 26 | 67 | "Wake" should read --Wako-- |
| 30 | 19 | "16" should read --6-- |
| 30 | 40 | "87: 194" should read --87:194-- |

Signed and Sealed this

Twenty-first Day of July, 1998

Attest:

Attesting Officer

BRUCE LEHMAN

Commissioner of Patents and Trademarks